US012808888B2

(12) United States Patent
Würtz et al.

(10) Patent No.: US 12,808,888 B2

(45) Date of Patent: Nov. 24, 2026

(54) METHOD FOR DETERMINING WHETHER A SUBJECT IS AT RISK OF DEVELOPING A MENTAL AND/OR A BEHAVIOURAL DISORDER

(71) Applicant: Nightingale Health Oyj, Helsinki (FI)

(72) Inventors: Peter Würtz, Helsinki (FI); Heli Julkunen, Helsinki (FI)

(73) Assignee: Nightingale Health Oyj, Helsinki (FI)

( * ) Notice: Subject to any disclaimer, the term of this patent is extended or adjusted under 35 U.S.C. 154(b) by 665 days.

(21) Appl. No.: 18/271,573

(22) PCT Filed: Jan. 7, 2022

(86) PCT No.: PCT/FI2022/050015

§ 371 (c)(1),
(2) Date: Jul. 10, 2023

(87) PCT Pub. No.: WO2022/148911

PCT Pub. Date: Jul. 14, 2022

(65) Prior Publication Data

US 2023/0393158 A1 Dec. 7, 2023

(30) Foreign Application Priority Data

Jan. 8, 2021 (FI) ..................................... 20215021

(51) Int. Cl.

| | |
|---|---|
| ***G01N 33/92*** | (2006.01) |
| ***G01N 24/08*** | (2006.01) |
| ***G01N 33/68*** | (2006.01) |

(52) U.S. Cl.

CPC ............. *G01N 33/92* (2013.01); *G01N 24/08* (2013.01); *G01N 33/6893* (2013.01); *G01N 2800/301* (2013.01); *G01N 2800/50* (2013.01)

(58) Field of Classification Search

CPC ............... G01N 24/08; G01N 2800/30; G01N 2800/301; G01N 2800/50; G01N 33/6893; G01N 33/92

See application file for complete search history.

(56) References Cited

U.S. PATENT DOCUMENTS

| | | | |
|---|---|---|---|
| 2012/0094315 | A1 | 4/2012 | Fryar-Williams |
| 2019/0120860 | A1 | 4/2019 | Rutherford et al. |

FOREIGN PATENT DOCUMENTS

| | | | |
|---|---|---|---|
| JP | 2011-506995 | A | 3/2011 |
| JP | 2020-532732 | A | 11/2020 |

(Continued)

OTHER PUBLICATIONS

WO 2017100879 translation (Year: 2017).*

(Continued)

*Primary Examiner* — Jennifer Wecker

(74) *Attorney, Agent, or Firm* — Haug Partners LLP; Wan Chieh Lee

(57) ABSTRACT

A method for determining whether a subject is at risk of developing a mental disorder; wherein the method comprises determining in a biological sample obtained from the subject a quantitative value of at lease one bio-marker of the following in the biological sample: glycoprotein acetyls, albumin, a ratio of docosahexaenoic acid to total fatty acids, a ratio of linoleic acid to total fatty acids, a ratio of monounsaturated fatty acids and/or of oleic acid to total fatty acids, a ratio of omega-3 fatty acids to total fatty acids, a ratio of omega-6 fatty acids to total fatty acids, a ratio of saturated fatty acids to total fatty acids, fatty acid degree of unsaturation, docosahexaenoic acid, linoleic acid, monounsaturated fatty acids and/or oleic acid, omega-3 fatty acids, omega-6 fatty acids, saturated fatty acids, triglycerides in high-density lipoprotein (HDL), triglycerides in low-density lipoprotein (LDL), high-density lipoprotein (HDL) particle (Continued)

size, low-density lipoprotein (LDL) particle size, very-low-density lipoprotein (VLDL) particle size, acetate, citrate, glutamine, histidine; and comparing the quantitative value(s) of the at least one biomarker to a control sample or to a control value; wherein an increase or a decrease in the quantitative value(s) of the at least one biomarker, when compared to the control sample or to the control value, is/are indicative of the subject having an increased risk of developing a mental disorder; wherein the at least one biomarker comprises or is glycoprotein acetyls, and wherein the mental disorder is anxiety disorder and/or reaction to severe stress disorder.

16 Claims, 24 Drawing Sheets

(56) References Cited

FOREIGN PATENT DOCUMENTS

| | | | | | |
|---|---|---|---|---|---|
| WO | WO-2007050318 | A2 | * | 5/2007 | ............ G01N 33/92 |
| WO | WO-2011010104 | A1 | * | 1/2011 | ......... G01N 33/6896 |
| WO | WO 2015/027116 | A1 | | 2/2015 | |
| WO | WO-2017100879 | A1 | * | 6/2017 | ............ G16B 40/00 |
| WO | WO-2020242976 | A1 | * | 12/2020 | ............... G06N 7/01 |
| WO | WO-2021089771 | A1 | * | 5/2021 | ......... G01N 33/6893 |
| WO | WO-2021186047 | A1 | * | 9/2021 | ............ G16H 50/50 |

OTHER PUBLICATIONS

Sudha, R. et al., "Serum zinc and copper levels in maintenance haemodialysis patients and its relationship with depression and anxiety", Global Journal of Medicine and Public Health, vol. 4, No. 3, 2015, pp. 1-7, https://www.gjmedph.com/Uploads/O2-Vo4No3.pdf.
Notice of Reasons for Rejection dated Oct. 7, 2025 issued in corresponding Japanese Patent Application No. 2023-538850 and its English Machine Translation.
Bot, M. et al., "Metabolomics Profile in Depression: A Pooled Analysis of 230 Metabolic Markers in 5283 Cases with Depression and 10,145 Controls." Biological Psychiatry, vol. 87, Issue 5, pp. 409-418 (Mar. 1, 2020).
De Kluiver H. et al., P. 721 Metabolomic profiles discriminating anxiety from depression, European Neuropsychopharmacology, Elsevier Science Publishers BV, Amsterdam, NL, vol. 40, Nov. 1, 2020 (Nov. 1, 2020), XP086353846.
Brunoni, A. R. et al., "Prospective associations between hsCRP and GlycA inflammatory biomarkers and depression: The Brazilian longitudinal study of adult health (Elsa-Brasil)," Journal of Affective Disorders., vol. 271, Jun. 1, 2020, pp. 39-48, XP055901866.
Poudel-Tandukar, K. et al., Serum albumin levels and depression in people living with Human Immunodeficiency Virus infection: a cross-sectional study. In: Journal of Psychosomatic Research, Oct. 2017, vol. 101, pp. 38-43.
Mcfarland, D. C. et al., Depression and Inflammation in Patients with Lung Cancer: A Comparative Analysis of Acute Phase Reactant Inflammatory Markers. In: Psychosomatics, Sep. 2020, vol. 61, Issue 5, pp. 527-537.
Carvalho C. M. et al., Investigating Causality Between Blood Metabolites and Emotional and Behavioral Responses to Traumatic Stress: a Mendelian Randomization Study, Molecular Neurobiology, 2020, vol. 57, pp. 1542-1552.
Carvalho C. M. et al., Metabolome-Wide Mendelian Randomization Analysis of Trauma Response. Biological Psychiatry, 2019, vol. 85, No. 10, Supplement, pp. S64-S65.
Yehuda, R. et al., Post-traumatic stress disorder. Nature Reviews Disease Primers, 2015, vol. 1, 15057, 1-22.
Tian, J.-S. et al., Discovery, screening and evaluation of a plasma biomarker panel for subjects with psychological suboptimal health state using 1H-NMR-based metabolomics profiles. Scientific Reports, 2016, vol. 6, 33820.
Kettunen, J. et al., Biomarker Glycoprotein Acetyls is Associated with the Risk of a Wide Spectrum of Incident Diseases and Stratifies Mortality Risk in Angiography Patients. Circulation: Genomic and Precision Medicine, 2018, vol. 11, No. 11, e002234, 1-7.
Connelly, M. A. et al., GlycA, a novel biomarker of systemic inflammation and cardiovascular disease risk, Journal of Translation Medicine, (2017) 15:219, 1-5.
Jula A. et al., Effects of Diet and Simvastatin on Fatty Acid Composition in Hypercholesterolemic Men, a Randomized Controlled Trial, Arterioscler Thromb Vasc Biol. 2005;25:1952-1959.
Julkunen H. et al., Atlas of plasma NMR biomarkers for health and disease in 118,461 individuals from the UK Biobank, Nature Communications (2023)14:604, 1-15.
Kettunen, J. et al., Genome-wide association study identifies multiple loci influencing human serum metabolite levels, Nat Genet.; 44(3): 269-276 (2013).
Ritchie. S. C. et al., The Biomarker GlycA is Associated with Chronic Inflammation and Predicts Long-Term Risk of Severe Infection, Cell Systems 1, 293-301, Oct. 28, 2015.
Soininen, P. et al., High-throughput serum NMR metabonomics for cost-effective holistic studies on systemic metabolism, Analyst, 2009, 134, 1781-1785.
Soininen, P. et al., Quantitative Serum Nuclear Magnetic Resonance Metabolomics in Cardiovascular Epidemiology and Genetics, Circ Cardiovasc Genet, Feb. 2015, 192-206.
Sudlow C. et al., UK Biobank: An Open Access Resource for Identifying the Causes of a Wide Range of Complex Diseases of Middle and Old Age, PLOS Medicine, 1-10, Mar. 31, 2015.
Würtz P. et al., Quantitative Serum Nuclear Magnetic Resonance Metabolomics in Large-Scale Epidemiology: A Primer on -Omic Technologies, Am J Epidemiol, 2017; 186(9):1084-1096.
International Search Report and Written Opinion mailed on May 16, 2022 in PCT International Application No. PCT/FI2022/050015.

* cited by examiner

F00−F99, T36−T50, X60−X84: Mental and behaviour disorders
9 710 events

F30−F39: Mood affective disorders (2656 events)

F30−F39: Mood affective disorders (2656 events)

F05: Delirium due to known physiological condition (543 events)

F05: Delirium due to known physiological condition (543 events)

F41: Other anxiety disorders (2013 events)

F41: Other anxiety disorders (2013 events)

R41: Other symptoms and signs involving cognitive functions and awareness (923 events)

R41: Other symptoms and signs involving cognitive functions and awareness (923 events)

METHOD FOR DETERMINING WHETHER A SUBJECT IS AT RISK OF DEVELOPING A MENTAL AND/OR A BEHAVIOURAL DISORDER

PRIORITY CLAIM

This application is the National Stage entry under 35 U.S.C. § 371 of International Application No. PCT/FI2022/050015, filed on Jan. 7, 2022, published on Jul. 14, 2022 under Publication Number WO 2022/148911 A1, which claims the benefit of priority under 35 U.S.C. § 119 of Finnish Patent Application Number FI 20215021 filed on Jan. 8, 2021, the entireties of which are herein incorporated by reference.

TECHNICAL FIELD

The present disclosure relates generally to methods for determining whether a subject is at risk of developing a mental and/or a behavioural disorder.

BACKGROUND

Mental and behavioural disorders are patterns of behavioral and/or psychological symptoms that impact multiple areas of life. These disorders cause substantial distress for the patients experiencing the symptoms and their families. Common mental disorders include, for instance, anxiety, depression, bipolar disorder and schizophrenia. Fortunately, there are effective strategies for preventing and treating many mental disorders. Early identification of individuals at an elevated risk of developing such disorders is important to provide early access to health care and social services, and to prevent the development of more serious conditions.

Various blood biomarkers may be useful for predicting whether an individual is at an elevated risk of developing various mental and/or behavioural disorders, such as mental disorders due to known physiological conditions, mood affective disorders, anxiety, dissociative, stress-related, somatoform and other nonpsychotic disorders, delirium, major depressive disorder, anxiety disorders and other symptoms and signs involving cognitive functions and awareness. Biomarkers predictive of the onset of these disorders would help to enable more effective screening and better targeted early treatment and prevention. Such biomarkers may be measured from biological samples, for example from blood samples or related biological fluids.

SUMMARY

A method for determining whether a subject is at risk of developing a mental and/or a behavioural disorder is disclosed. The method may comprise determining in a biological sample obtained from the subject a quantitative value of at least one biomarker of the following:

- albumin,
- glycoprotein acetyls,
- a ratio of docosahexaenoic acid to total fatty acids,
- a ratio of linoleic acid to total fatty acids,
- a ratio of monounsaturated fatty acids and/or of oleic acid to total fatty acids,
- a ratio of omega-3 fatty acids to total fatty acids,
- a ratio of omega-6 fatty acids to total fatty acids,
- a ratio of saturated fatty acids to total fatty acids,
- fatty acid degree of unsaturation,
- docosahexaenoic acid,
- linoleic acid,
- monounsaturated fatty acids and/or oleic acid,
- omega-3 fatty acids,
- omega-6 fatty acids,
- saturated fatty acids,
- triglycerides in high-density lipoprotein (HDL),
- triglycerides in low-density lipoprotein (LDL),
- high-density lipoprotein (HDL) particle size,
- low-density lipoprotein (LDL) particle size,
- very-low-density lipoprotein (VLDL) particle size,
- acetate,
- citrate,
- glutamine,
- histidine; and comparing the quantitative value(s) of the at least one biomarker to a control sample or to a control value;

wherein an increase or a decrease in the quantitative value(s) of at least one biomarker, when compared to the control sample or to the control value, is/are indicative of the subject having an increased risk of developing the mental and/or the behavioural disorder.

BRIEF DESCRIPTION OF THE DRAWINGS

The accompanying drawings, which are included to provide a further understanding of the embodiments and constitute a part of this specification, illustrate various embodiments. In the drawings.

DETAILED DESCRIPTION

Figure 1A:
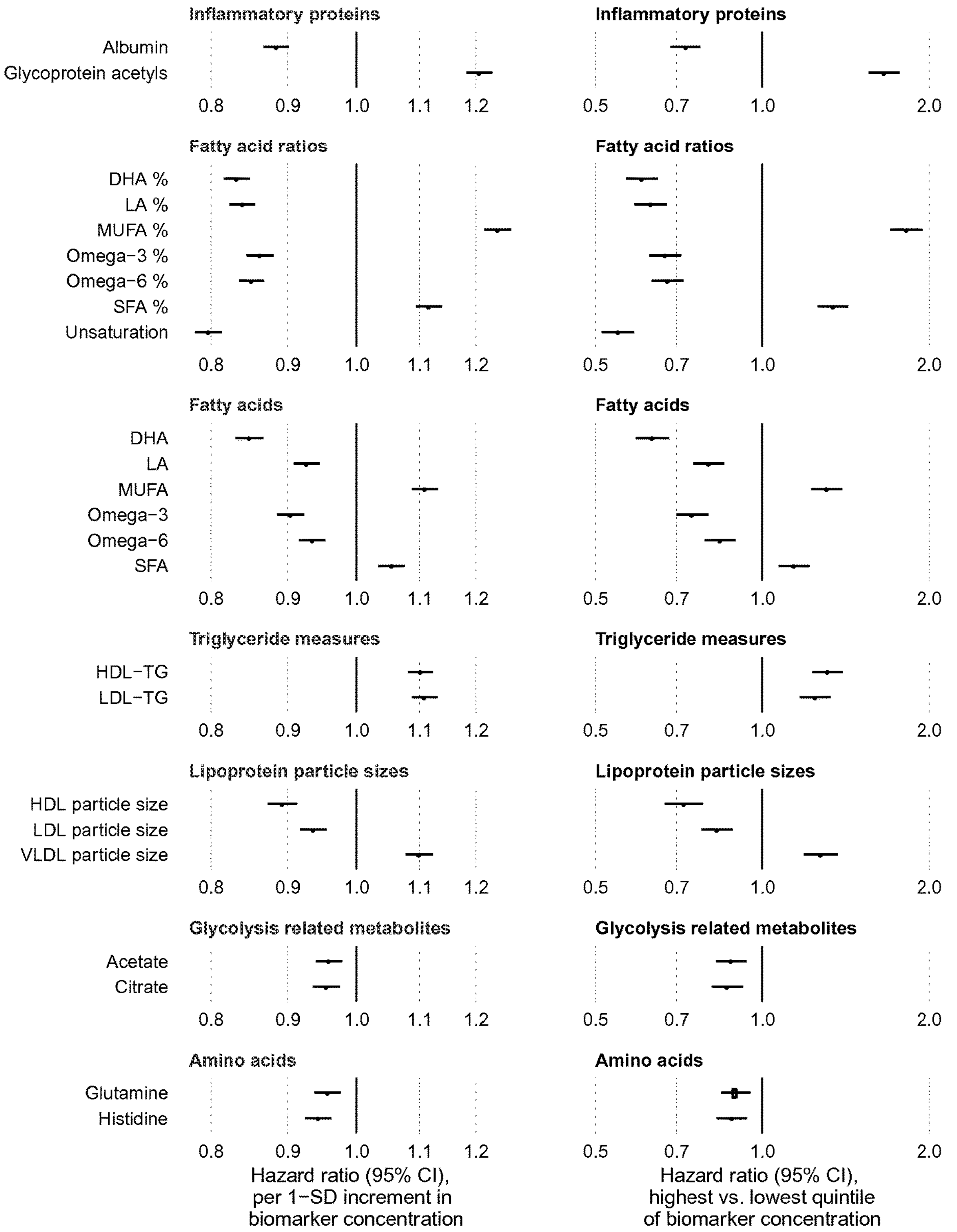
FIG. 1*a* shows the relation of baseline concentrations of 24 blood biomarkers to the future development of Any Mental and/or Behavioural Disorder (defined as the combined endpoint of any ICD-10 diagnoses within F00-F99, T36-T50, X60-X84; here termed "Any Mental and/or Behavioural Disorder"), when the biomarker concentrations are analysed in absolute concentrations and in quintiles of biomarker concentrations. Results are based on plasma samples from approximately 115 000 generally healthy individuals from the UK Biobank.

A method for determining whether a subject is at risk of developing a mental and/or a behavioural disorder is disclosed.

The method may comprise determining in a biological sample obtained from the subject a quantitative value of at least one biomarker of the following:

- albumin,
- glycoprotein acetyls,
- a ratio of docosahexaenoic acid to total fatty acids,
- a ratio of linoleic acid to total fatty acids,
- a ratio of monounsaturated fatty acids and/or of oleic acid to total fatty acids,
- a ratio of omega-3 fatty acids to total fatty acids,
- a ratio of omega-6 fatty acids to total fatty acids,
- a ratio of saturated fatty acids to total fatty acids,
- fatty acid degree of unsaturation,
- docosahexaenoic acid,
- linoleic acid,
- monounsaturated fatty acids and/or oleic acid,
- omega-3 fatty acids,
- omega-6 fatty acids,
- saturated fatty acids,
- triglycerides in high-density lipoprotein (HDL),
- triglycerides in low-density lipoprotein (LDL),
- high-density lipoprotein (HDL) particle size,
- low-density lipoprotein (LDL) particle size,
- very-low-density lipoprotein (VLDL) particle size,
- acetate,
- citrate,
- glutamine,
- histidine; and
- and comparing the quantitative value(s) of the at least one biomarker to a control sample or to a control value;
- wherein an increase or a decrease in the quantitative value(s) of the at least one biomarker, when compared to the control sample or to the control value, is/are indicative of the subject having an increased risk of developing the mental and/or the behavioural disorder.

Various blood biomarkers may be useful for predicting whether an individual person is at elevated risk of developing a broad range of mental and/or behavioural disorders. Such biomarkers may be measured from biological samples, for example from blood samples or related biological fluids. Biomarkers predictive of mental and/or behavioural disorders could help to enable more effective screening and better targeted preventative treatment.

In an embodiment, the method comprises determining a quantitative value of albumin.

In an embodiment, the method comprises determining a quantitative value of glycoprotein acetyls.

In an embodiment, the method comprises determining a quantitative value of the ratio of docosahexaenoic acid to total fatty acids.

In an embodiment, the method comprises determining a quantitative value of the ratio of linoleic acid to total fatty acids.

In an embodiment, the method comprises determining a quantitative value of the ratio of monounsaturated fatty acids and/or oleic acid to total fatty acids.

In an embodiment, the method comprises determining a quantitative value of the ratio of omega-3 fatty acids to total fatty acids.

In an embodiment, the method comprises determining a quantitative value of the ratio of omega-6 fatty acids to total fatty acids.

In an embodiment, the method comprises determining a quantitative value of the ratio of saturated fatty acids to total fatty acids.

In an embodiment, the method comprises determining a quantitative value of fatty acid degree of unsaturation.

In an embodiment, the method comprises determining a quantitative value of docosahexaenoic acid.

In an embodiment, the method comprises determining a quantitative value of linoleic acid.

In an embodiment, the method comprises determining a quantitative value of monounsaturated fatty acids and/or oleic acid.

In an embodiment, the method comprises determining a quantitative value of omega-3 fatty acids.

In an embodiment, the method comprises determining a quantitative value of omega-6 fatty acids.

In an embodiment, the method comprises determining a quantitative value of saturated fatty acids.

In an embodiment, the method comprises determining a quantitative value of triglycerides in high-density lipoprotein (HDL).

In an embodiment, the method comprises determining a quantitative value of triglycerides in low-density lipoprotein (LDL).

In an embodiment, the method comprises determining a quantitative value of high-density lipoprotein (HDL) particle size.

In an embodiment, the method comprises determining a quantitative value of low-density lipoprotein (LDL) particle size.

In an embodiment, the method comprises determining a quantitative value of very-low-density lipoprotein (VLDL) particle size.

In an embodiment, the method comprises determining a quantitative value of acetate.

In an embodiment, the method comprises determining a quantitative value of citrate.

In an embodiment, the method comprises determining a quantitative value of glutamine.

In an embodiment, the method comprises determining a quantitative value of histidine.

The metabolic biomarker(s) described in this specification have been found to be significantly different, i.e. their quantitative values (such as amount and/or concentration) have been found to be significantly higher or lower, for subjects who later developed a mental and/or a behavioural disorder. The biomarkers may be detected and quantified from blood, serum, or plasma, dry blood spots, or other suitable biological sample, and may be used to determine the risk of developing a mental and/or a behavioural disorder, either alone or in combination with other biomarkers.

Furthermore, the biomarker(s) may significantly improve the possibility of identifying subjects at risk for a mental and/or a behavioural disorder, even in combination with and/or when accounting for established risk factors that may currently be used for screening and risk prediction, such as age, sex, smoking status, use of alcohol and/or recreational drugs, body mass index (BMI), ongoing medical conditions, traumatic experiences, life situations and conflicts, social isolation, socioeconomic factors, genetic risk and/or prior medical and/or family history of having mental and/or behavioural disorders and/or other comorbidities. The biomarkers described in this specification, alone or as a risk score (such as a multi-biomarker score), hazard ratio, odds ratio, and/or predicted absolute or relative risk, or in combination with other risk factors and tests, may improve prediction or even replace the need for other tests or measures. This may include improving prediction accuracy by complementing the predictive information from other risk factors, or by replacing the need for other analyses, such as physical examinations, psychological evaluations and/or laboratory tests such as checks for thyroid function and/or use of alcohol and/or drugs. The biomarkers or the risk score, hazard ratio, odds ratio, and/or predicted absolute or relative risk according to one or more embodiments described in this specification may thus allow for efficiently assessing the risk for future development of a mental and/or a behavioural disorder, also in conditions in which other risk factor measures are not as feasible.

In an embodiment, the method is a method for determining whether the subject is at risk of developing a mental and/or a behavioural disorder.

The method may comprise determining in the biological sample quantitative values of a plurality of the biomarkers, such as two, three, four, five or more biomarkers. For example, the plurality of the biomarkers may comprise 2, 3, 4, 5, 6, 7, 8, 9, 11, 12, 13, 14, 15, 16, 17, 18, 19, 20, 21, 22, 23 or 24 (i.e. at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23 or all) of the biomarkers. The term "plurality of the biomarkers" may thus, within this specification, be understood as referring to any number (above one) of the biomarkers. The term "plurality of the biomarkers" may thus be understood as referring to any number (above one) and/or combination or subset of the biomarkers described in this specification. Determining the plurality of the biomarkers may increase the accuracy of the prediction of whether the subject is at risk of developing a mental and/or a behavioural disorder. In general, it may be that the higher the number of the biomarkers, the more accurate or predictive the method. However, even a single biomarker described in this specification may allow for or assist in determining whether the subject is at risk of developing a mental and/or a behavioural disorder. The plurality of the biomarkers may be measured from the same biological sample or from separate biological samples and using the same analytical method or different analytical methods. In an embodiment, the plurality of biomarkers may be a panel of a plurality of biomarkers.

In the context of this specification, the wording "comparing the quantitative value(s) of the biomarker(s) to a control sample or to a control value(s)" may be understood, as a skilled person would, as referring to comparing the quantitative value or values of the biomarker or biomarkers, to a control sample or to a control value(s) either individually or as a plurality of biomarkers (e.g. when a risk score is calculated from the quantitative values of a plurality of biomarkers), depending e.g. on whether the quantitative value of a single (individual) biomarker or the quantitative values of a plurality of biomarkers are determined.

In an embodiment, the method may comprise determining in the biological sample obtained from the subject a quantitative value or quantitative values of the following biomarkers:

albumin,
glycoprotein acetyls,
the ratio of docosahexaenoic acid to total fatty acids,
the ratio of linoleic acid to total fatty acids,
the ratio of monounsaturated fatty acids and/or of oleic acid to total fatty acids,
the ratio of omega-3 fatty acids to total fatty acids,
the ratio of omega-6 fatty acids to total fatty acids,
the ratio of saturated fatty acids to total fatty acids,
fatty acid degree of unsaturation,
docosahexaenoic acid,
linoleic acid,
monounsaturated fatty acids and/or oleic acid,
omega-3 fatty acids,
omega-6 fatty acids,
saturated fatty acids,
triglycerides in high-density lipoprotein (HDL),
triglycerides in low-density lipoprotein (LDL),
high-density lipoprotein (HDL) particle size,
low-density lipoprotein (LDL) particle size,
very-low-density lipoprotein (VLDL) particle size,
acetate,
citrate,
glutamine,
histidine; and
comparing the quantitative value(s) of the biomarkers to a control sample or to a control value(s);
wherein an increase or a decrease in the quantitative value(s) of the biomarkers, when compared to the control sample or to the control value, is/are indicative of the subject having an increased risk of developing a mental and/or a behavioural disorder.

In an embodiment, at least one biomarker comprises or is glycoprotein acetyls. The method may further comprise determining a quantitative value of at least one of the other biomarkers described in this specification.

The subject may be human. The human may be healthy or have an existing disease, such as an existing mental and/or behavioural disorder. Specifically, the human may have an already existing form of a mental and/or a behavioural disorder, and the risk for developing a more severe form of the disorder and/or of another mental and/or behavioural disorder or other mental and/or behavioural disorders may be determined and/or calculated. The subject may, additionally or alternatively, be an animal, such as a mammal, for example, a non-human primate, a dog, a cat, a horse, or a rodent.

In the context of this specification, the term "biomarker" may refer to a biomarker, for example a chemical or molecular marker, that may be found to be associated with a disease or a condition or the risk of having or developing thereof. It does not necessarily refer to a biomarker that would be statistically fully validated as having a specific effectiveness in a clinical setting. The biomarker may be a metabolite, a compound, a lipid, a protein, a moiety, a functional group, a composition, a combination of two or more metabolites and/or compounds, a (measurable or measured) quantity thereof, a ratio or other value derived thereof, or in principle any measurement reflecting a chemical and/or biological component that may be found associated with a disease or condition or the risk of having or developing thereof. The biomarkers and any combinations thereof, optionally in combination with further analyses and/or measures, may be used to measure a biological process indicative of the risk for developing a mental and/or a behavioural disorder, such as mood affective disorders, anxiety, dissociative, stress-related, somatoform and other nonpsychotic disorders, delirium, major depressive disorder, anxiety disorders and other symptoms and signs involving cognitive functions and awareness.

The disorder may refer to a category of mental and/or behavioural disorders or to a specific disorder in this category. In the context of this specification, the term "a mental and/or a behavioural disorder" may be understood as referring to diseases, disorders and/or conditions with behavioral and/or psychological symptoms. The disorder may be acute or occasional, or a chronic condition, which in the context of this specification may be understood as persistent or otherwise long-lasting in its effects and/or a disease that comes with time. The signs and symptoms of mental and/or behavioral disorders may vary from mild to severe or disabling, depending on factors such as age and/or overall health of the subject.

The biomarker associations may be similar for the different mental and/or behavioural disorders. Therefore, the same individual biomarkers and combinations of biomarkers may be extended to also predict the risk for specific mental and/or behavioural disorders. Examples of such specific mental and/or behavioural disorders may include mood affective disorders, anxiety, dissociative, stress-related, somatoform and other nonpsychotic disorders, delirium, major depressive disorder, anxiety disorders and other symptoms and signs involving cognitive functions and awareness.

Mental and/or behavioural disorders described in this specification may be classified as follows. "ICD-10" may be understood as referring to the International Statistical Classification of Diseases and Related Health Problems 10th Revision (ICD-10)—WHO Version for 2019. Similar diseases classified or diagnosed by other disease classification systems than ICD-10, such as ICD-9 or ICD-11, may also apply.

The term "Any Mental and/or Behavioural Disorder" may be understood as referring to any mental and/or behavioural disease, disorder or condition. Any Mental and/or Behavioural Disorder (or "mental and/or behavioural disorder") may be understood as referring to any incident occurrence of ICD-10 diagnoses F00-F99, T36-T50 and/or X60-X84.

Mental and/or Behavioural Disorder Subgroups may be understood as referring to diseases and/or conditions classified within the ICD-10 subchapter diagnoses for mental and/or behavioural disorders (F01-F09, F30-F29, F30-F39, F40-F48, T36-T50, X60-X84).

Specific mental and/or behavioural disorders may be understood as referring to diseases and/or disorders classified within the 3-character ICD-10 diagnoses for mental and/or behavioural disorders (F05, F06, F20, F31, F32, F33, F40, F41, F43, R41, T39, T40, T42, T43).

In an embodiment, the mental and/or the behavioural disorder is a subgroup of mental and/or behavioural disorders, such as a subgroup defined by one or more ICD-10 subchapters described in this specification.

In an embodiment, the mental and/or the behavioural disorder is a specific disease, such as a specific disease or disorder defined by a ICD-10 3-character code diagnosis.

In an embodiment, the mental and/or the behavioural disorder is a disease or disorder among one or more of the following mental and/or behavioural disorder subgroups:

F01-F09: Mental disorders due to known physiological conditions
F20-F29: Schizophrenia, schizotypal, delusional, and other non mood psychotic disorders
F30-F39: Mood [affective] disorders
F40-F48: Anxiety, dissociative, stress related, somatoform and other nonpsychotic mental disorders T36-T50: Poisoning by, adverse effects of and underdosing of drugs, medicaments and biological substances X60-X84: Intentional self-harm In an embodiment, the mental and/or the behavioural disorder is one of the following ICD-10 3-character diagnoses or selected from disorders of the following ICD-10 3-character diagnoses:

F05: Delirium due to known physiological condition

F06: Other mental disorders due to known physiological condition

F20: Schizophrenia

F31: Bipolar disorder

F32: Major depressive disorder, single episode

F33: Major depressive disorder, recurrent

F40: Phobic anxiety disorders

F41: Other anxiety disorders

F43: Reaction to severe stress, and adjustment disorders

R41: Other symptoms and signs involving cognitive functions and awareness

T39: Poisoning by, adverse effect of and underdosing of nonopioid analgesics, antipyretics and antirheumatics T40: Poisoning by, adverse effect of and underdosing of narcotics and psychodysleptics [hallucinogens]

T42: Poisoning by, adverse effect of and underdosing of antiepileptic, sedative- hypnotic and antiparkinsonism drugs T43: Poisoning by, adverse effect of and underdosing of psychotropic drugs, not elsewhere classified In an embodiment, the mental and/or the behavioural disorder may comprise or be death from a mental and/or a behavioural disorder, such as a disorder denoted by the ICD-10 codes listed above, including poisoning and intentional self-harm.

In an embodiment, the mental and/or the behavioural disorder may comprise or be a mental disorder due to known physiological conditions (F01-F09); schizophrenia, schizotypal, delusional, and/or other non mood psychotic disorder (F20-F29); mood [affective] disorder (F30-F39); anxiety, dissociative, stress related, somatoform and/or other nonpsychotic mental disorder (F40-F48); poisoning by, adverse effect of and/or underdosing of drugs, medicaments and/or biological substances (T36-T50); and/or intentional self-harm (X60-X84).

In an embodiment, the mental and/or the behavioural disorder may comprise or be delirium due to known physiological condition (F05); other mental disorder due to known physiological condition (F06); schizophrenia (F20); bipolar disorder (F31); major depressive disorder, single episode (F32); major depressive disorder, recurrent (F33); phobic anxiety disorder (F40); other anxiety disorder (F41); reaction to severe stress, and/or an adjustment disorder (F43); other symptom or sign involving cognitive functions and awareness (R41); poisoning by, adverse effect of and/or underdosing of nonopioid analgesics, antipyretics and/or antirheumatics (T39); poisoning by, adverse effect of and/or underdosing of narcotics and psychodysleptics [hallucinogens] (T40); poisoning by, adverse effect of and/or underdosing of antiepileptic, sedative- hypnotic and/or antiparkinsonism drugs (T42); and/or poisoning by, adverse effect of and/or underdosing of psychotropic drugs, not elsewhere classified (T43).

In an embodiment, the mental and/or the behavioural disorder may comprise or be a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

The method may further comprise determining whether the subject is at risk of developing a mental and/or a behavioural disorder using a risk score, hazard ratio, and/or predicted absolute or relative risk calculated on the basis of the quantitative value(s) of the at least one biomarker or of the plurality of the biomarkers.

An increase or a decrease in the risk score, hazard ratio, and/or predicted absolute risk and/or relative risk may be indicative of the subject having an increased risk of developing the mental and/or the behavioural disorder.

The risk score and/or hazard ratio and/or predicted absolute risk or relative risk may be calculated based on any plurality, combination or subset of biomarkers described in this specification.

The risk score and/or hazard ratio and/or predicted absolute risk or relative risk may be calculated e.g. as shown in the Examples below. For example, the plurality of biomarkers measured using a suitable method, for example with NMR spectroscopy, may be combined using regression algorithms and multivariate analyses and/or using machine learning analysis. Before regression analysis or machine learning, any missing values in the biomarkers may be imputed with the mean value of each biomarker for the dataset. A number of biomarkers, for example five, that may be considered most associated with the onset of the disease or condition may be selected for use in the prediction model. Other modelling approaches may be used to calculate a risk score and/or hazard ratio and/or predicted absolute risk or relative risk based on a combination or subset of individual biomarkers, i.e. a plurality of the biomarkers.

The risk score may be calculated e.g. as a weighted sum of individual biomarkers, i.e. a plurality of the biomarkers. The weighted sum may be e.g. in the form of a multi-biomarker score defined as $\Sigma_i [\![ \beta_i * c_i ]\!] + \beta_0$; where i is the index of summation over individual biomarkers, $\beta_i$ is the weighted coefficient attributed to biomarker i, $c_i$ is the blood concentration of biomarker i, and $\beta_0$ is an intercept term.

For example, the risk score can be defined as: $\beta_1$*concentration(glycoprotein acetyls)+$\beta_2$*concentration (monounsaturated fatty acid ratio to total fatty acids)+$\beta_3$*concentration(albumin)+$\beta_0$, where $\beta_1$, $\beta_2$, $\beta_3$ are multipliers for each biomarker according to the association magnitude with risk of a mental and/or a behavioural disorder and $\beta_0$ is an intercept term. As a skilled person will understand, the biomarkers mentioned in this example may be replaced by any other biomarker(s) described in this specification. In general, the more biomarkers are included in the risk score, the stronger the predictive performance may become. When additional biomarkers are included in the risk score, the $\beta_i$ weights may change for all biomarkers according to the optimal combination for the prediction of a mental and/or a behavioural disorder.

The risk score, hazard ratio, odds ratio, and/or predicted relative risk and/or absolute risk may be calculated on the basis of at least one further measure, for example a characteristic of the subject. Such characteristics may be determined prior to, simultaneously, or after the biological sample is obtained from the subject. As a skilled person will understand, some of the characteristics may be information collected e.g. using a questionnaire or clinical data collected earlier. Some of the characteristics may be determined (or may have been determined) by biochemical or clinical diagnostic measurements and/or medical diagnosis. Such characteristics could include, for example, one or more of age, height, weight, body mass index, race or ethnic group, smoking, and/or family history of mental and/or behavioural disorders.

The method may further comprise administering a treatment to the subject at risk of developing a mental and/or a behavioural disorder to thereby treat the subject in order to prevent or treat the disease in the subject. The risk prediction for a mental and/or a behavioural disorder guided based on one or more of the biomarkers can be used to guide preventative efforts, such as psychotherapy, alcohol and smoking awareness, healthy diet, sufficient sleep, physical activity and/or clinical screening frequency and/or pharmacological treatment decisions. For example, the information of the future risk for a mental and/or a behavioural disorder can be used for guiding psychological care, psychosocial interventions, psychiatric treatment or treatment with, for instance, cholinesterase inhibitors, antidepressants, pychosomatic medicine, and/or mood stabilizers and stimulants.

In the context of this specification, the term "albumin" may be understood as referring to serum albumin (often referred to as blood albumin). It is an albumin found in vertebrate blood. Albumin is a globular, water-soluble, unglycosylated serum protein of approximate molecular weight of 65,000 Daltons. The measurement of albumin using NMR is described e.g. in publications by Kettunen et al., 2012, Nature Genetics 44, 269-276; Soininen et al., 2015, Circulation: Cardiovascular Genetics 8, 212-206 (DOI: 10.1161/CIRCGENETICS.114.000216). Albumin may also be measured by various other methods, for example by clinical chemistry analyzers. Examples of such methods may include e.g. dye-binding methods such as bromocresol green and bromocresol purple.

In the context of this specification, the term "glycoprotein acetyls", "glycoprotein acetylation", or "GlycA" may refer to the abundance of circulating glycated proteins, and/or to a nuclear magnetic resonance spectroscopy (NMR) signal that represents the abundance of circulating glycated proteins, i.e. N-acetylated glycoproteins. Glycoprotein acetyls may include signals from a plurality of different glycoproteins, including e.g. alpha-1-acid glycoprotein, alpha-1 antitrypsin, haptoglobin, transferrin, and/or alpha-1 antichymotrypsin. In the scientific literature on cardiometabolic biomarkers, the terms "glycoprotein acetyls" or "GlycA" may commonly refer to the NMR signal of circulating glycated proteins (e.g. Ritchie et al, Cell Systems 2015 1(4):293-301; Connelly et al, J Transl Med. 2017;15(1): 219). Glycoprotein acetyls and a method for measuring them is described e.g. in Kettunen et al., 2018, Circ Genom Precis Med. 11:e002234 and Soininen et al., 2009, Analyst 134, 1781-1785. There may be benefits of using the NMR signal of glycoprotein acetyls for risk prediction above measurement of the individual proteins contributing to the NMR signal, for instance better analytical accuracy and stability over time, as well as lower costs of the measurement and the possibility to measure the NMR signal simultaneously with many other biomarkers.

In the context of this specification, the term "omega-3 fatty acids" may refer to total omega-3 fatty acids, i.e. the total omega-3 fatty acid amounts and/or concentrations, i.e. the sum of different omega-3 fatty acids. Omega-3 fatty acids are polyunsaturated fatty acids. In omega-3 fatty acids, the last double bond in the fatty acid chain is the third bond counting from the methyl end. Docosahexaenoic acid is an example of an omega-3 fatty acid.

In the context of this specification, the term "omega-6 fatty acids" may refer to total omega-6 fatty acids, i.e. the total omega-6 fatty acid amounts and/or concentrations, i.e. the sum of the amounts and/or concentrations of different omega-6 fatty acids. Omega-6 fatty acids are polyunsaturated fatty acids. In omega-6 fatty acids, the last double bond in the fatty acid chain is the sixth bond counting from the methyl end.

In one embodiment, the omega-6 fatty acid may be linoleic acid. Linoleic acid (18:2ω-6) is the most abundant type of omega-6 fatty acids, and may therefore be considered as a good approximation for total omega-6 fatty acids for risk prediction of a mental and/or a behavioural disorder.

In the context of this specification, the term "monounsaturated fatty acids" (MUFAs) may refer to total monounsaturated fatty acids, i.e. the total MUFA amounts and/or concentrations. Monounsaturated fatty acids may, alternatively, refer to oleic acid, which is the most abundant monounsaturated fatty acid in human serum. Monounsaturated fatty acids have one double bond in their fatty acid chain. The monounsaturated fatty acids may include omega-9 and omega-7 fatty acids. Oleic acid (18:1ω-9), palmitoleic acid (16:1ω-7) and cis-vaccenic acid (18:1ω-7) are examples of common monounsaturated fatty acids in human serum.

In one embodiment, the monounsaturated fatty acid may be oleic acid. Oleic acid is the most abundant monounsaturated fatty acid, and may therefore be considered as a good approximation for total monounsaturated fatty acids for risk prediction of a mental and/or a behavioural disorder.

In the context of this specification, the term "saturated fatty acids" (SFAs) may refer to total saturated fatty acids. Saturated fatty acids may be or comprise fatty acids which have no double bonds in their structure. Palmitic acid (16:0) and stearic acid (18:0) are examples of abundant SFAs in human serum.

For all fatty acid measures, including omega-6, docosahexaenoic acid, linoleic acid, monounsaturated fatty acids and/or saturated fatty acids, the fatty acid measures may include blood (or serum/plasma) free fatty acids, bound fatty acids and esterified fatty acids. Esterified fatty acids may, for example, be esterified to glycerol as in triglycerides, diglycerides, monoglycerides, or phosphoglycerides, or to cholesterol as in cholesterol esters.

In the context of this specification, the term "fatty acid degree of unsaturation" or "unsaturation" may be understood as referring to the number of double bonds in total fatty acids, for example the average number of double bonds in total fatty acids.

In the context of this specification, the term "HDL" refers to high-density lipoprotein.

In the context of this specification, the term "LDL" refers to low-density lipoprotein.

In the context of this specification, the term "VLDL" refers to very-low-density lipoprotein.

In the context of this specification, the phrase "low-density lipoprotein (LDL) triglycerides", "high-density lipoprotein (HDL) triglycerides", "triglycerides in HDL (high-density lipoprotein)", or "triglycerides in LDL (low-density lipoprotein)", may be understood as referring to total triglyceride concentration in said lipoprotein class or subfraction.

In the context of this specification, the phrase "high-density lipoprotein (HDL) particle size", "low-density lipoprotein (LDL) particle size", or "very-low-density lipoprotein (VLDL) particle size", may be understood as referring to the average diameter for the particles in said lipoprotein class or subfraction.

In the context of this specification, the term "acetate" may refer to the acetate molecule and/or acetic acid, for example in blood, plasma or serum or related biofluids.

In the context of this specification, the term "citrate" may refer to the citrate molecule and/or citric acid, for example in blood, plasma or serum or related biofluids.

In the context of this specification, the term "glutamine" may refer to the glutamine amino acid, for example in blood, plasma or serum or related biofluids.

In the context of this specification, the term "histidine" may refer to the histidine amino acid, for example in blood, plasma or serum or related biofluids.

In the context of this specification, the term "quantitative value" may refer to any quantitative value characterizing the amount and/or concentration of a biomarker. For example, it may be the amount or concentration of the biomarker in the biological sample, or it may be a signal derived from nuclear magnetic resonance spectroscopy (NMR) or other method suitable for detecting the biomarker in a quantitative manner. Such a signal may be indicative of or may correlate with the amount or concentration of the biomarker. It may also be a quantitative value calculated from one or more signals derived from NMR measurements or from other measurements. Quantitative values may, additionally or alternatively, be measured using a variety of techniques. Such methods may include mass spectrometry (MS), gas chromatography combined with MS, high performance liquid chromatography alone or combined with MS, immunoturbidimetric measurements, ultracentrifugation, ion mobility, enzymatic analyses, colorimetric or fluorometric analyses, immunoblot analysis, immunohistochemical methods (e.g. in situ methods based on antibody detection of metabolites), and immunoassays (e.g. ELISA). Examples of various methods are set out below. The method used to determine the quantitative value(s) in the subject may be the same method that is used to determine the quantitative value(s) in a control subject/control subjects or in a control sample/control samples.

The quantitative value, or the initial quantitative value, of the at least one biomarker, or the plurality of the biomarkers, may be measured using nuclear magnetic resonance (NMR) spectroscopy, for example $^{1}$H-NMR. The at least one additional biomarker, or the plurality of the additional biomarkers, may also be measured using NMR. NMR may provide a particularly efficient and fast way to measure biomarkers, including a large number of biomarkers simultaneously, and can provide quantitative values for them. NMR also typically requires very little sample pre-treatment or preparation. The biomarkers measured with NMR can effectively be measured for large amounts of samples using an assay for blood (serum or plasma) NMR metabolomics previously published by Soininen et al., 2015, Circulation: Cardiovascular Genetics 8, 212-206 (DOI: 10.1161/CIRCGENETICS.114.000216); Soininen et al., 2009, Analyst 134, 1781-1785; and Würtz et al., 2017, American Journal of Epidemiology 186 (9), 1084-1096 (DOI: 10.1093/aje/kwx016). This provides data on 250 biomarkers per sample as described in detail in the above scientific papers.

In an embodiment, the (initial) quantitative value of the at least one biomarker is/are measured using nuclear magnetic resonance spectroscopy.

However, quantitative values for various biomarkers described in this specification may also be performed by techniques other than NMR. For example, mass spectrometry (MS), enzymatic methods, antibody-based detection methods, or other biochemical or chemical methods may be contemplated, depending on the biomarker.

For example, glycoprotein acetyls can be measured or approximated by immunoturbidimetric measurements of alpha-1-acid glycoprotein, haptoglobin, alpha-1-antitrypsin, and transferrin (e.g. as described in Ritchie et al., 2015, Cell Syst. 28;1(4):293-301).

E.g. monounsaturated fatty acids, saturated fatty acids, and omega-6 fatty acids can be quantified (i.e. their quantitative values may be determined) by serum total fatty acid composition using gas chromatography (for example, as described in Jula et al., 2005, Arterioscler Thromb Vasc Biol 25, 2152-2159).

In the context of this specification, the term "sample" or "biological sample" may refer to any biological sample obtained from a subject or a group or population of subjects. The sample may be fresh, frozen, or dry.

The biological sample may comprise or be, for example, a blood sample, a plasma sample, a serum sample, or a sample derived therefrom. The biological sample may be, for example, a fasting blood sample, a fasting plasma sample, a fasting serum sample, or a fraction obtainable therefrom. However, the biological sample does not necessarily have to be a fasting sample. The blood sample may be a venous blood sample.

The blood sample may be a dry blood sample. The dry blood sample may be a dried whole blood sample, a dried plasma sample, a dried serum sample, or a dried sample derived therefrom.

The method may comprise obtaining the biological sample from the subject prior to determining the quantitative value of the at least one biomarker. Taking a blood sample or a tissue sample of a subject or patient is a part of normal clinical practice. The collected blood or tissue sample can be prepared and serum or plasma can be separated using techniques well known to a skilled person. Methods for separating one or more fractions from biological samples, such as blood samples or tissue samples, are also available to a skilled person. The term "fraction" may, in the context of this specification, also refer to a portion or a component of the biological sample separated according to one or more physical properties, for instance solubility, hydrophilicity or hydrophobicity, density, or molecular size.

In the context of this specification, the term "control sample" may refer to a sample obtained from a subject and known not to suffer from the disease or condition or not being at risk of having or developing the disease or condition. The control sample may be matched. In an embodiment, the control sample may be a biological sample from a healthy individual or a generalized population of healthy individuals. The term "control value" may be understood as a value obtainable from the control sample or control samples and/or a quantitative value derivable therefrom. For example, it may be possible to calculate a threshold value from control samples and/or control values, above or below which the risk of developing the disease or condition is elevated. In other words, a value higher or lower (depending on the biomarker, risk score, hazard ratio, and/or predicted absolute risk or relative risk) than the threshold value may be indicative of the subject having an increased risk of developing the disease or condition.

An increase or a decrease in the quantitative value(s) of the at least one biomarker, or the plurality of the biomarkers, when compared to the control sample or to the control value, may be indicative of the subject having an increased risk of having or developing the disease or condition. Whether an increase or a decrease is indicative of the subject having an increased risk of developing the disease or condition, may depend on the biomarker.

A 1.2-fold, 1.5-fold, or for example 2-fold, or 3-fold, increase or a decrease in the quantitative value(s) of the at least one biomarker (or in an individual biomarker of the plurality of the biomarkers) when compared to the control sample or to the control value, may be indicative of the subject having an increased risk of developing the disease or condition.

In an embodiment, a decrease in the quantitative value of albumin, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of glycoprotein acetyls, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of ratio of docosahexaenoic acid to total fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of ratio of linoleic acid to total fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of ratio of monounsaturated fatty acids and/or oleic acid to total fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of ratio of omega-3 fatty acids to total fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of ratio of omega-6 fatty acids to total fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of ratio of saturated fatty acids to total fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of fatty acid degree of unsaturation, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of docosahexaenoic acid, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of linoleic acid, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of monounsaturated fatty acids and/or oleic acid, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of omega-3 fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of omega-6 fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of saturated fatty acids, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of triglycerides in high-density lipoprotein (HDL), when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of triglycerides in low-density lipoprotein (LDL), when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of high-density lipoprotein (HDL) particle size, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of low-density lipoprotein (LDL) particle size, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, an increase in the quantitative value of very-low-density lipoprotein (VLDL) particle size, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of acetate, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of citrate, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of glutamine, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a decrease in the quantitative value of histidine, when compared to the control sample or to the control value, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a risk score defined as $\beta_0+\beta_1$*concentration (glycoprotein acetyls)+$\beta_2$* concentration (albumin), where $\beta_0$ is an intercept term, $\beta_1$ is the weighted coefficient attributed to the concentration of glycoprotein acetyls, and $\beta_2$ is the weighted coefficient attributed to the concentration of albumin, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.

In an embodiment, a risk score defined as $\beta_0+\beta_1$*concentration (glycoprotein acetyls)+$\beta_2$* concentration (fatty acid measure), where $\beta_0$ is an intercept term, $\beta_1$ is the weighted coefficient attributed to the concentration of glycoprotein acetyls, $\beta_2$ is the weighted coefficient attributed to the fatty acid measure, may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive functions and/or awareness. The fatty acid measure may be one or more of the following fatty acids or their ratio to total fatty acids: docosahexaenoic acid, linoleic acid, omega-3 fatty acids, omega-6 fatty acids, monounsaturated fatty acids, saturated fatty acids and/or fatty acid degree of unsaturation.

In an embodiment, a risk score defined as $\beta_0+\beta_1$*concentration (glycoprotein acetyls)+$\beta_2$* concentration (albumin)+$\beta_3$*concentration (fatty acid measure), where $\beta_0$ is an intercept term, $\beta_1$ is the weighted coefficient attributed to the concentration of glycoprotein acetyls, $\beta_2$ is the weighted coefficient attributed to the concentration of albumin, and $\beta_3$ is the weighted coefficient attributed to the concentration of the fatty acid measure may be indicative of the subject having an increased risk of developing a mental and/or a behavioural disorder, such as a mood affective disorder, anxiety, dissociative, stress-related, somatoform and/or other nonpsychotic disorder, delirium, major depressive disorder, anxiety disorder, and/or other symptom and/or sign involving cognitive function and/or awareness. The fatty acid measure may be one or more of the following fatty acids or their ratio to total fatty acids: docosahexaenoic acid, linoleic acid, omega-3 fatty acids, omega-6 fatty acids, monounsaturated fatty acids, saturated fatty acids and/or fatty acid degree of unsaturation.

The term "combination" may, at least in some embodiments, be understood such that the method comprises using a risk score, hazard ratio, odds ratio, and/or predicted absolute risk or relative risk calculated on the basis of the quantitative value(s) of the biomarkers. For example, if quantitative values of both glycoprotein acetyls and albumin are determined, the quantitative values of both biomarkers may be compared to the control sample or the control value separately, or a risk score, hazard ratio, odds ratio, and/or predicted absolute risk or relative risk calculated on the basis of the quantitative value(s) of both the biomarkers, and the risk score, hazard ratio, odds ratio, and/or predicted absolute risk or relative risk may be compared to the control sample or the control value.

In an embodiment, the method may comprise determining in the biological sample obtained from the subject a quantitative value of the following biomarkers:

glycoprotein acetyls;

albumin; and comparing the quantitative value(s) of the biomarkers and/or a combination thereof to a control sample or to a control value(s);

wherein an increase or a decrease in the quantitative value(s) of the biomarkers and/or the combination thereof, when compared to the control sample or to the control value, is/are indicative of the subject having an increased risk of developing the mental and/or the behavioural disorder. An increase in the quantitative value of glycoprotein acetyls and a decrease in the quantitative value of albumin, when compared to the control sample or to the control value, may be indicative of the subject having an increased risk of developing the mental and/or the behavioural disorder.

In an embodiment, the method may comprise determining in the biological sample obtained from the subject a quantitative value of the following biomarkers:

glycoprotein acetyls, at least one fatty acid measure(s) of the following fatty acids or their ratio to total fatty acids: docosahexaenoic acid, linoleic acid, omega-3 fatty acids, omega-6 fatty acids, monounsaturated fatty acids, saturated fatty acids and/or fatty acid degree of unsaturation; and comparing the quantitative value(s) of the biomarkers and/or a combination thereof to a control sample or to a control value(s);

wherein an increase or a decrease in the quantitative value(s) of the biomarkers and/or the combination thereof, when compared to the control sample or to the control value, is/are indicative of the subject having an increased risk of developing the mental and/or the behavioural disorder. An increase in the quantitative value of glycoprotein acetyls and a decrease in the quantitative value of docosahexaenoic and/or linoleic acid and/or omega-3 fatty acids and/or omega-6 fatty acids and/or fatty acid degree of unsaturation and/or their ratio to total fatty acids, and/or an increase in the quantitative value of monounsaturated fatty acids and/or saturated fatty acids and/or their ratio to total fatty acids, when compared to the control sample or to the control value, may be indicative of the subject having an increased risk of developing the mental and/or the behavioural disorder.

In an embodiment, the method may comprise determining in the biological sample obtained from the subject a quantitative value of the following biomarkers:

albumin, at least one fatty acid measure(s) of the following fatty acids or their ratio to total fatty acids: docosahexaenoic acid, linoleic acid, omega-3 fatty acids, omega-6 fatty acids, monounsaturated fatty acids, saturated fatty acids and/or fatty acid degree of unsaturation; and comparing the quantitative value(s) of the biomarkers and/or a combination thereof to a control sample or to a control value(s);

wherein an increase or a decrease in the quantitative value(s) of the biomarkers and/or the combination thereof, when compared to the control sample or to the control value, is/are indicative of the subject having an increased risk of developing the mental and/or the behavioural disorder. A decrease in the quantitative value of albumin and a decrease in the quantitative value of docosahexaenoic and/or linoleic acid and/or omega-3 fatty acids and/or omega-6 fatty acids and/or fatty acid degree of unsaturation and/or their ratio to total fatty acids, and/or an increase in the quantitative value of monounsaturated fatty acids and/or saturated fatty acids and/or their ratio to total fatty acids, when compared to the control sample or to the control value, may be indicative of the subject having an increased risk of developing the mental and/or the behavioural disorder.

In an embodiment, the method may comprise determining in the biological sample obtained from the subject a quantitative value of the following biomarkers:

glycoprotein acetyls, albumin, at least one fatty acid measure(s) of the following fatty acids or their ratio to total fatty acids: docosahexaenoic acid, linoleic acid, omega-3 fatty acids, omega-6 fatty acids, monounsaturated fatty acids, saturated fatty acids and/or fatty acid degree of unsaturation; and comparing the quantitative value(s) of the biomarkers and/or a combination thereof to a control sample or to a control value(s);

wherein an increase or a decrease in the quantitative value(s) of the biomarkers and/or the combination thereof, when compared to the control sample or to the control value, is/are indicative of the subject having an increased risk of developing the mental and/or the behavioural disorder. An increase in the quantitative value of glycoprotein acetyls, a decrease in the quantitative value of albumin and a decrease in the quantitative value of docosahexaenoic and/or linoleic acid and/or omega-3 fatty acids and/or omega-6 fatty acids and/or fatty acid degree of unsaturation and/or their ratio to total fatty acids, and/or an increase in the quantitative value of monounsaturated fatty acids and/or saturated fatty acids and/or their ratio to total fatty acids, when compared to the control sample or to the control value, may be indicative of the subject having an increased risk of developing the mental and/or the behavioural disorder.

The following embodiments are disclosed:

1. A method for determining whether a subject is at risk of developing a mental and/or a behavioural disorder;

wherein the method comprises determining in a biological sample obtained from the subject a quantitative value of at least one biomarker of the following in the biological sample:

albumin,
glycoprotein acetyls,
a ratio of docosahexaenoic acid to total fatty acids,
a ratio of linoleic acid to total fatty acids,
a ratio of monounsaturated fatty acids and/or of oleic acid to total fatty acids,
a ratio of omega-3 fatty acids to total fatty acids,
a ratio of omega-6 fatty acids to total fatty acids,
a ratio of saturated fatty acids to total fatty acids,
fatty acid degree of unsaturation,
docosahexaenoic acid,
linoleic acid,
monounsaturated fatty acids and/or oleic acid,
omega-3 fatty acids,
omega-6 fatty acids,
saturated fatty acids,
triglycerides in high-density lipoprotein (HDL),
triglycerides in low-density lipoprotein (LDL),
high-density lipoprotein (HDL) particle size,
low-density lipoprotein (LDL) particle size,
very-low-density lipoprotein (VLDL) particle size,
acetate,
citrate,
glutamine,
histidine; and comparing the quantitative value(s) of the at least one biomarker to a control sample or to a control value;

wherein an increase or a decrease in the quantitative value(s) of the at least one biomarker, when compared to the control sample or to the control value, is/are indicative of the subject having an increased risk of developing a mental and/or a behavioural disorder.

2. The method according to embodiment 1, wherein the method comprises determining in the biological sample quantitative values of a plurality of the biomarkers, such as two, three, four, five or more biomarkers.
3. The method according to any one of embodiments 1 - 2, wherein the at least one biomarker comprises or is glycoprotein acetyls.
4. The method according to any one of embodiments 1 - 3, wherein the method comprises determining in the biological sample obtained from the subject a quantitative value of the following biomarkers:

glycoprotein acetyls;
albumin; and comparing the quantitative value(s) of the biomarkers to a control sample or to a control value(s);

wherein an increase or a decrease in the quantitative value(s) of the biomarkers, when compared to the control sample or to the control value, is/are indicative of the subject having an increased risk of developing a mental and/or a behavioural disorder.

5. The method according to any one of embodiments 1 - 4, wherein the method comprises determining in the biological sample obtained from the subject a quantitative value of the following biomarkers:

glycoprotein acetyls, at least one fatty acid measure(s) of the following: ratio of docosahexaenoic acid to total fatty acids, docosahexaenoic acid, ratio of linoleic acid to total fatty acids, linoleic acid, ratio of monounsaturated fatty acids and/or of oleic acid to total fatty acids, ratio of omega-6 fatty acids to total fatty acids, omega-6 fatty acids, ratio of saturated fatty acids to total fatty acids, saturated fatty acids, fatty acid degree of unsaturation; and comparing the quantitative value(s) of the biomarkers to a control sample or to a control value(s);

wherein an increase or a decrease in the quantitative value(s) of the biomarkers, when compared to the control sample or to the control value, is/are indicative of the subject having an increased risk of developing a mental and/or a behavioural disorder.

6. The method according to any one of embodiments 1-5, wherein the mental and/or the behavioural disorder comprises or is a mental disorder due to known physiological conditions (F01-F09); schizophrenia, schizotypal, delusional, and/or other non mood psychotic disorder (F20-F29); mood [affective] disorder (F30-F39); anxiety, dissociative, stress related, somatoform and/or other nonpsychotic mental disorder (F40-F48); poisoning by, adverse effect of and/or underdosing of drugs, medicaments and/or biological substances (T36-T50); and/or intentional self-harm (X60-X84).
7. The method according to any one of embodiments 1-6, wherein the mental and/or the behavioural disorder comprises or is delirium due to known physiological condition (F05); other mental disorder due to known physiological condition (F06); schizophrenia (F20); bipolar disorder (F31); major depressive disorder, single episode (F32); major depressive disorder, recurrent (F33); phobic anxiety disorder (F40); other anxiety disorder (F41); reaction to severe stress, and/or adjustment disorder (F43); other symptom and/or sign involving cognitive functions and/or awareness (R41); poisoning by, adverse effect of and/or underdosing of nonopioid analgesics, antipyretics and/or antirheumatics (T39); poisoning by, adverse effect of and/or underdosing of narcotics and/or psychodysleptics [hallucinogens] (T40); poisoning by, adverse effect of and/or underdosing of antiepileptic, sedative- hypnotic and/or antiparkinsonism drugs (T42); and/or poisoning by, adverse effect of and/or underdosing of psychotropic drugs, not elsewhere classified (T43).
8. The method according to any one of embodiments 1-7, wherein the mental and/or the behavioural disorder comprises or is a mood affective disorder, anxiety, dissociative, stress-related, somatoform and/or other nonpsychotic disorder, delirium, major depressive disorder, anxiety disorder, and/or other symptom and/or sign involving cognitive functions and/or awareness.
9. The method according to any one of embodiments 1-8, wherein the quantitative value of the at least one biomarker is/are measured using nuclear magnetic resonance spectroscopy.

The method according to any one of embodiments 1-9, wherein the method further comprises determining whether the subject is at risk of developing a mental and/or a behavioural disorder using a risk score, hazard ratio, odds ratio, and/or predicted absolute risk or relative risk calculated on the basis of the quantitative value(s) of the at least one biomarker or of the plurality of the biomarkers.

EXAMPLES

Reference will now be made in detail to various embodiments, an example of which is illustrated in the accompanying drawings. The description below discloses some embodiments in such a detail that a person skilled in the art is able to utilize the embodiments based on the disclosure. Not all steps or features of the embodiments are discussed in detail, as many of the steps or features will be obvious for the person skilled in the art based on this specification.

Abbreviations used in the Figures:

DHA %: Ratio of docosahexaenoic acid to total fatty acids
LA%: Ratio of linoleic acid to total fatty acids
MUFA %: Ratio of monounsaturated fatty acids to total fatty acids
Omega-3%: Ratio of omega-3 fatty acids to total fatty acids
Omega-6%: Ratio of omega-6 fatty acids to total fatty acids
SFA %: Ratio of saturated fatty acids to total fatty acids
DHA: Docosahexaenoic acid
LA: Linoleic acid
MUFA: Monounsaturated fatty acids
Omega-6: Omega-6 fatty acids
Omega-3: Omega-3 fatty acids
SFA: Saturated fatty acids
Unsaturation: Fatty acid degree of unsaturation
HDL: High-density lipoprotein
LDL: Low-density lipoprotein
VLDL: Very-low-density lipoprotein
HDL-TG: Triglycerides in high-density lipoprotein (HDL)
LDL-TG: Triglycerides in low-density lipoprotein (HDL)
CI: confidence interval
SD: standard deviation
BMI: Body mass index

EXAMPLE 1

Biomarker measures quantified by nuclear magnetic resonance (NMR) were investigated as to whether they could be predictive of a mental and/or a behavioural disorder, such as mood affective disorders, anxiety, dissociative, stress-related, somatoform and other nonpsychotic disorders, delirium, major depressive disorder, anxiety disorders and other symptoms and signs involving cognitive functions and awareness. All analyses were conducted based on the UK Biobank, with approximately 115 000 study participants with blood biomarker data from NMR spectroscopy available.

Study Population

Details of the design of the UK Biobank have been reported by Sudlow et al 2015, PLoS Med. 2015;12(3): e1001779. Briefly, UK Biobank recruited 502 639 participants aged 37-73 years in 22 assessment centres across the UK. All participants provided written informed consent and ethical approval was obtained from the North West Multi-Center Research Ethics Committee. Blood samples were drawn at baseline between 2007 and 2010. No selection criteria were applied to the sampling.

Biomarker Profiling

From the entire UK Biobank population, a random subset of baseline plasma samples from 118 466 individuals were measured using the Nightingale NMR biomarker platform (Nightingale Health Ltd, Finland). This blood analysis method provides simultaneous quantification of many blood biomarkers, including lipoprotein lipids, circulating fatty acids, and various low-molecular weight metabolites including amino acids, ketone bodies and gluconeogenesis-related metabolites in molar concentration units. Technical details and epidemiological applications have been reviewed (Soininen et al 2015, Circ Cardiovasc Genet; 2015;8:192-206; Würtz et al 2017, Am J Epidemiol 2017;186:1084-1096). Values outside four interquartile ranges from median were considered as outliers and excluded.

Epidemiological Analyses of Biomarker Relations with the Risk of a Mental and/or a Behavioural Disorder The blood biomarker associations with the risk for a mental and/or a behavioural disorder were conducted based on UK Biobank data. Analyses focused on the relation of the biomarkers to the occurrence of a mental and/or a behavioural disorder after the blood samples were collected, to determine if the individual biomarkers associate with the risk for future development of a mental and/or a behavioural disorder. Examples using multi-biomarker scores, in the form weighted sums of biomarkers, were also explored to see if they could be predictive even more strongly than each individual biomarker.

Information on the disease events occurring after the blood samplings for all study participants were recorded from UK Hospital Episode Statistics data and death registries. All analyses are based on first occurrence of diagnosis, so that individuals with recorded diagnosis of the given disease prior to blood sampling were omitted from the statistical analyses. A composite endpoint of Any Mental and/or Behavioural Disorder was defined based on any incident occurrence of ICD-10 diagnoses FOO-F99, T36-T50 or X60-X84. More refined subtypes of the mental and/or the behavioural disorders were defined according to the ICD-10 diagnoses listed in Table 1.

The registry-based follow-up was from blood sampling in 2007-2010 through to 2020 (approximately 1 100 000 person-years). Specific diseases which had <100 disease events recorded during follow-up were left out of scope.

For biomarker association testing, Cox proportional-hazard regression models adjusted for age, sex, and UK Biobank assessment centre were used. Results were plotted in magnitudes per standard deviation of each biomarker measure to allow direct comparison of association magnitudes.

Summary of Results

Baseline characteristics of the study population for biomarker analyses vs future risk of a mental and/or a behavioural disorder are shown in Table 1. The number of incident disease events occurring after the blood sampling is listed for all the conditions analysed.

TABLE 1

Clinical characteristics of study participants and the number of incident disease events analysed.

| | |
|---|---|
| Total number of individuals with blood samples analysed | 118456 |
| Study setting | Population sample of study volunteers from the UK |

TABLE 1-continued

Clinical characteristics of study participants and the number of incident disease events analysed.

| | |
|---|---|
| Percentage of women | 54.1% |
| Age range (years) | 39-71 |
| Median age (years) | 58 |
| Median BMI (kg/m2) | 26.8 |
| Follow-up time for disease events after blood sampling | 10-14 years |
| Diseases with similar biomarker relations | Number of individuals who developed the specified disease after the blood sampling |
| Any Mental and/or Behavioural Disorder: any occurrence of F00-F99, T36-T50 or X60-X84 ICD-10 codes | 9716 |
| Mental and/or Behavioural Disorder Subgroups (defined by ICD-10 subchapters) | |
| F01-F09: Mental disorders due to known physiological conditions | 1817 |
| F20-F29: Schizophrenia, schizotypal, delusional, and other non mood psychotic disorders | 266 |
| F30-F39: Mood [affective] disorders | 5288 |
| F40-F48: Anxiety, dissociative, stress related, somatoform and other nonpsychotic mental disorders | 4366 |
| T36-T50: Poisoning by, adverse effects of and underdosing of drugs, medicaments and biological substances | 534 |
| X60-X84: Intentional self-harm | 260 |
| Specific Mental and/or Behavioural Disorders (defined by 3-character ICD-10 codes) | |
| F05: Delirium due to known physiological condition | 1052 |
| F06: Other mental disorders due to known physiological condition | 169 |
| F20: Schizophrenia | 126 |
| F31: Bipolar disorder | 263 |
| F32: Major depressive disorder, single episode | 5166 |
| F33: Major depressive disorder, recurrent | 131 |
| F40: Phobic anxiety disorders | 447 |
| F41: Other anxiety disorders | 3857 |
| F43: Reaction to severe stress, and adjustment disorders | 142 |
| R41: Other symptoms and signs involving cognitive functions and awareness | 1806 |
| T39: Poisoning by, adverse effect of and underdosing of nonopioid analgesics, antipyretics and antirheumatics | 223 |
| T40: Poisoning by, adverse effect of and underdosing of narcotics and psychodysleptics [hallucinogens] | 179 |
| T42: Poisoning by, adverse effect of and underdosing of antiepileptic, sedative- hypnotic and antiparkinsonism drugs | 114 |
| T43: Poisoning by, adverse effect of and underdosing of psychotropic drugs, not elsewhere classified | 159 |

FIG. 1*a* shows the hazard ratios for the 24 blood biomarkers with the future risk of Any Mental and/or Behavioural Disorder (ICD-10 codes F00-F99, T36-T50 OR X60-X84). The left-hand side of the figure shows the hazard ratios when the biomarkers are analysed in absolute concentrations, scaled to standard deviations of the study population. The right-hand side shows the corresponding hazard ratios when individuals in the highest quintile of the biomarker concentration are compared to those in the lowest quintile. The results are based on statistical analyses of over 115 000 individuals from the UK Biobank, out of whom 9 710 developed a mental and/or a behavioural disorder (defined as diagnoses F00-F99, T36-T50 OR X60-X84 in the hospital registries, or in the death records) during approximately 10 years of follow-up. The analyses were adjusted for age, sex, and UK Biobank assessment centre in Cox proportional-hazard regression models. P-values were P<0.0001 (corresponding to multiple testing correction) for all associations. These results demonstrate that the 24 individual biomarkers are predictive of the risk for a mental and/or a behavioural disorder in general population settings.

Figure 1B:
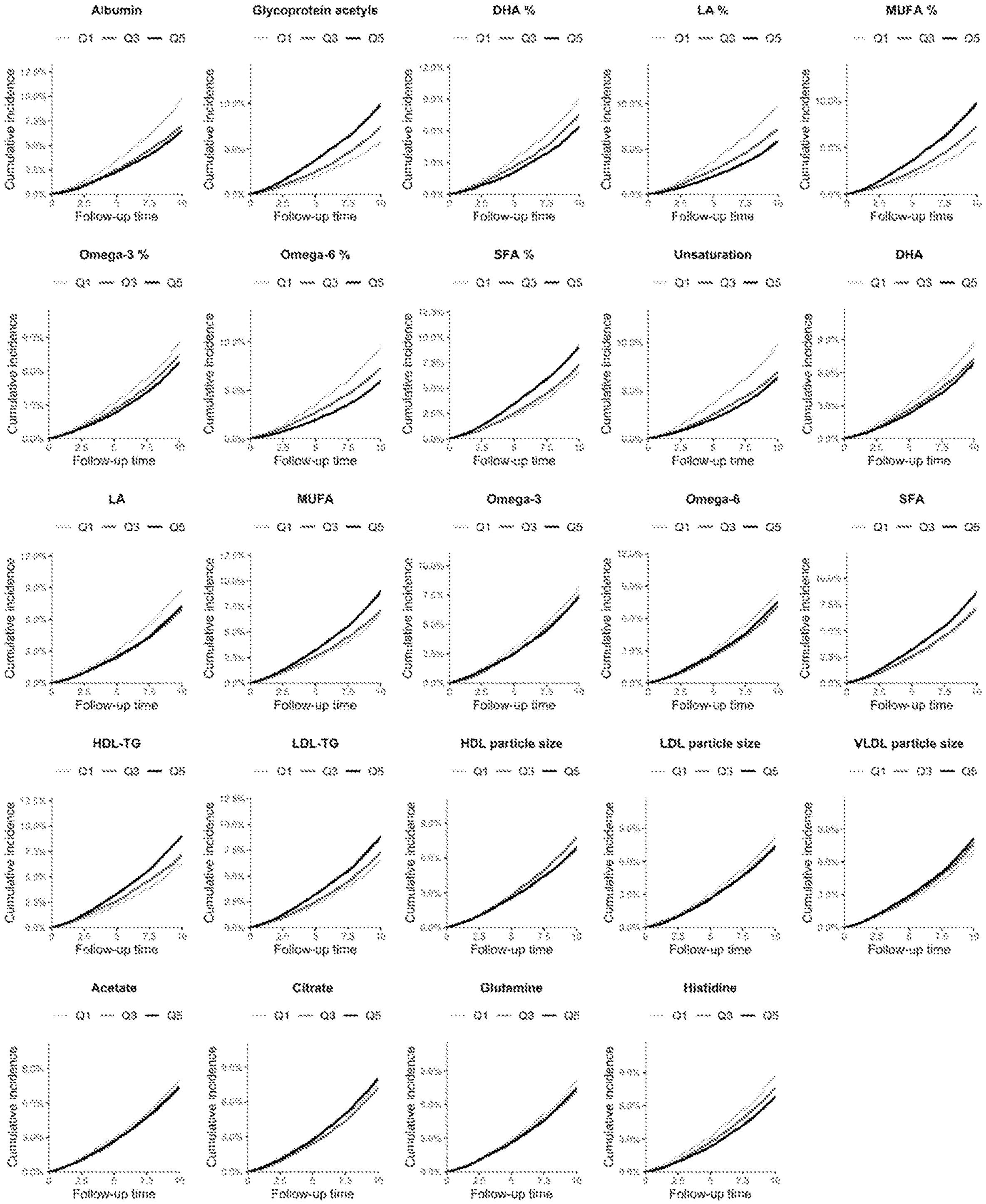
FIG. 1*b* shows the cumulative risk for "Any Mental and/or Behavioural Disorder" during follow-up for the lowest, middle, and highest quintiles of the 24 blood biomarker concentrations.

FIG. 1*b* shows the Kaplan-Meier plots of the cumulative risk for a mental and/or a behavioural disorder for each of the 24 blood biomarkers according to the lowest, middle, and highest quintiles of biomarker concentrations. The results are based on statistical analyses of over 115 000 individuals from the UK Biobank, out of whom 9 716 developed a mental and/or a behavioural disorder. These results further demonstrate that the 24 individual biomarkers are predictive of the risk for a mental and/or a behavioural disorder in general population settings.

Figure 2A:
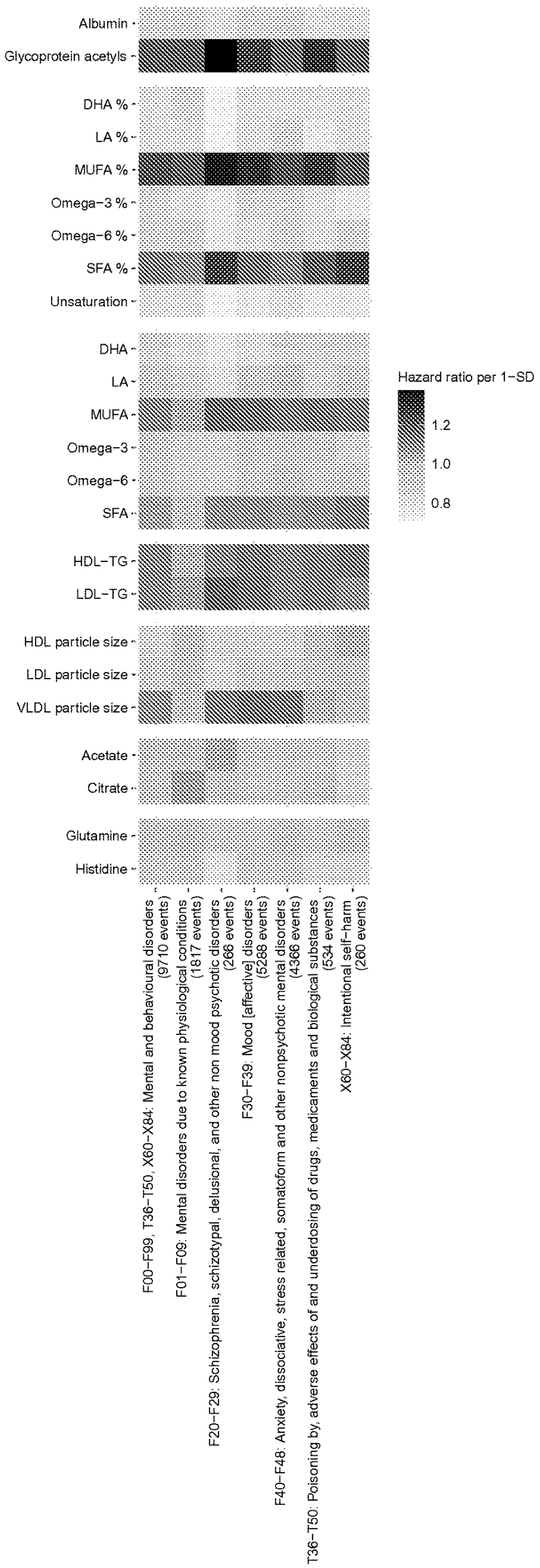
FIG. 2*a* shows the relation of the baseline concentrations of the 24 blood biomarkers to future development of 6 different categories of mental and/or behavioural disorders (defined by ICD-10 subchapters), in the form of a heatmap. The results demonstrate that the 6 different mental and/or behavioural disorder subgroups all have highly similar associations with the 24 biomarkers measured by nuclear magnetic resonance (NMR) spectroscopy of plasma samples from generally healthy humans.

FIG. 2*a* shows the hazard ratios for the 24 blood biomarkers for the future onset of 6 subgroups of mental and/or behavioural disorders, defined by ICD-10 subchapters. The results illustrate that the pattern of biomarker associations is highly consistent for the 6 different subtypes of mental and/or behavioural disorders.

Figure 2B:
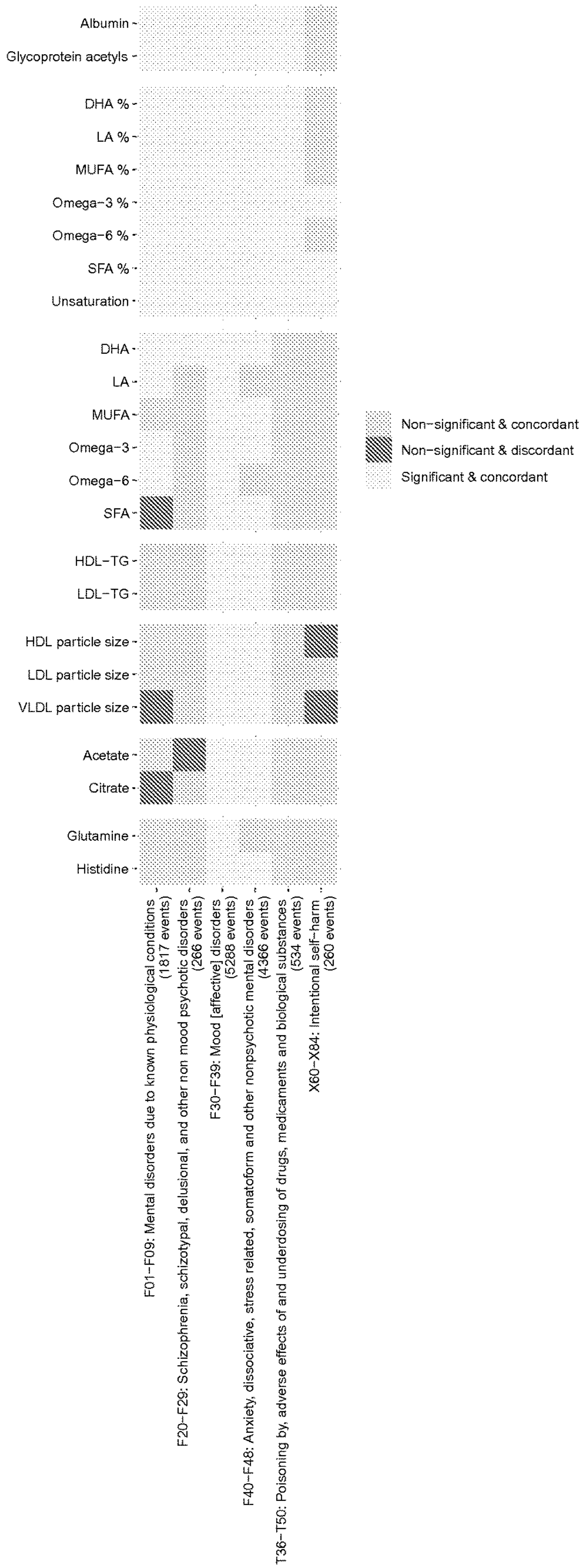
FIG. 2*b* shows the consistency of the biomarker associations with the 6 different categories of mental and/or behavioural disorders, defined by ICD-10 subchapters, in comparison to the direction of corresponding biomarker associations with "Any Mental and/or Behavioural Disorder".

FIG. 2*b* shows the consistency of the biomarker associations with the 6 mental and/or behavioural disorder subgroups (defined by ICD-10 subchapters) compared to the "Any Mental and/or Behavioural Disorder" definition. The biomarker associations were all in the same direction of association as for "Any Mental and/or Behavioural Disorder" or not statistically significant in the discordant direction. Any biomarker combination that strongly predicts "Any Mental and/or Behavioural Disorder" will therefore also be predictive of all the listed mental and/or behavioural disorder subgroups.

Figure 3A:
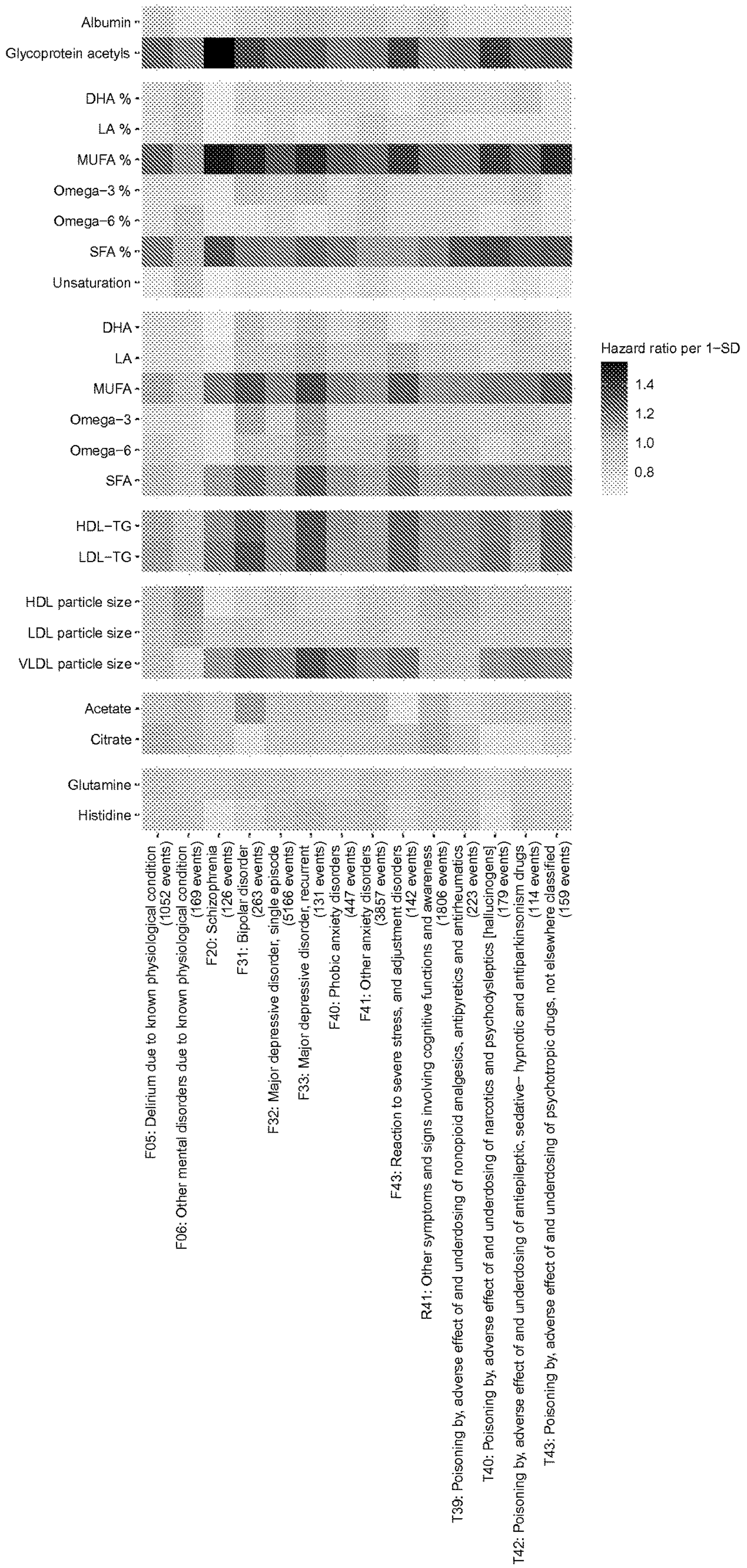
FIG. 3*a* shows the relation of baseline biomarker levels to the future development of 14 specific mental and/or behavioural disorders (defined by ICD-10 3-character diagnoses) in the form of a heatmap. The results demonstrate that the specific mental and/or behavioural disorders defined by 3-character ICD-10 codes all have highly similar associations with a broad panel of biomarkers measured by NMR spectroscopy of plasma samples from generally healthy humans.

FIG. 3*a* shows the hazard ratios for the 24 blood biomarkers for future onset of 14 specific mental and/or behavioural disorders, defined by 3-character ICD-10 diagnosis codes. The results illustrate that the pattern of biomarker associations is highly consistent for all the 14 specific disorders.

Figure 3B:
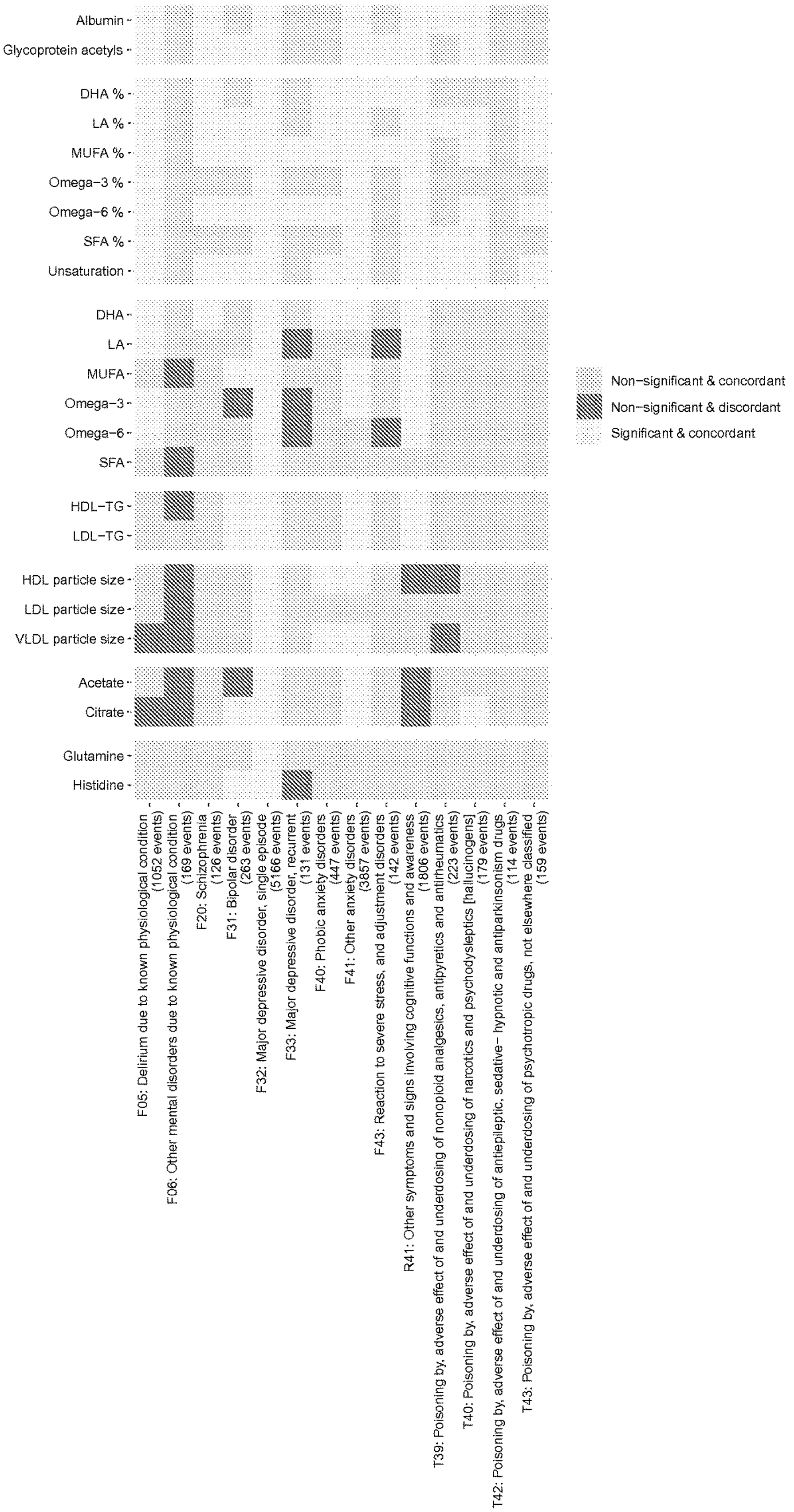
FIG. 3*b* shows the consistency of the biomarker associations with specific mental and/or behavioural disorders (defined by ICD-10 3-character diagnoses), in comparison to direction of the association with "Any Mental and/or Behavioural Disorder".

FIG. 3*b* shows the consistency of the biomarker associations with the 14 specific mental and/or behavioural disorders (defined by 3-character ICD-10 diagnosis codes) compared to the "Any Mental and/or Behavioural Disorder" definition. Generally, the biomarker associations are all in the same direction of association as for "Any Mental and/or Behavioural Disorder" or not statistically significant in the discordant direction. Any biomarker combination that strongly predicts "Any Mental and/or Behavioural Disorder" will therefore also be predictive of all the listed specific mental and/or behavioural disorders.

Figure 4A:
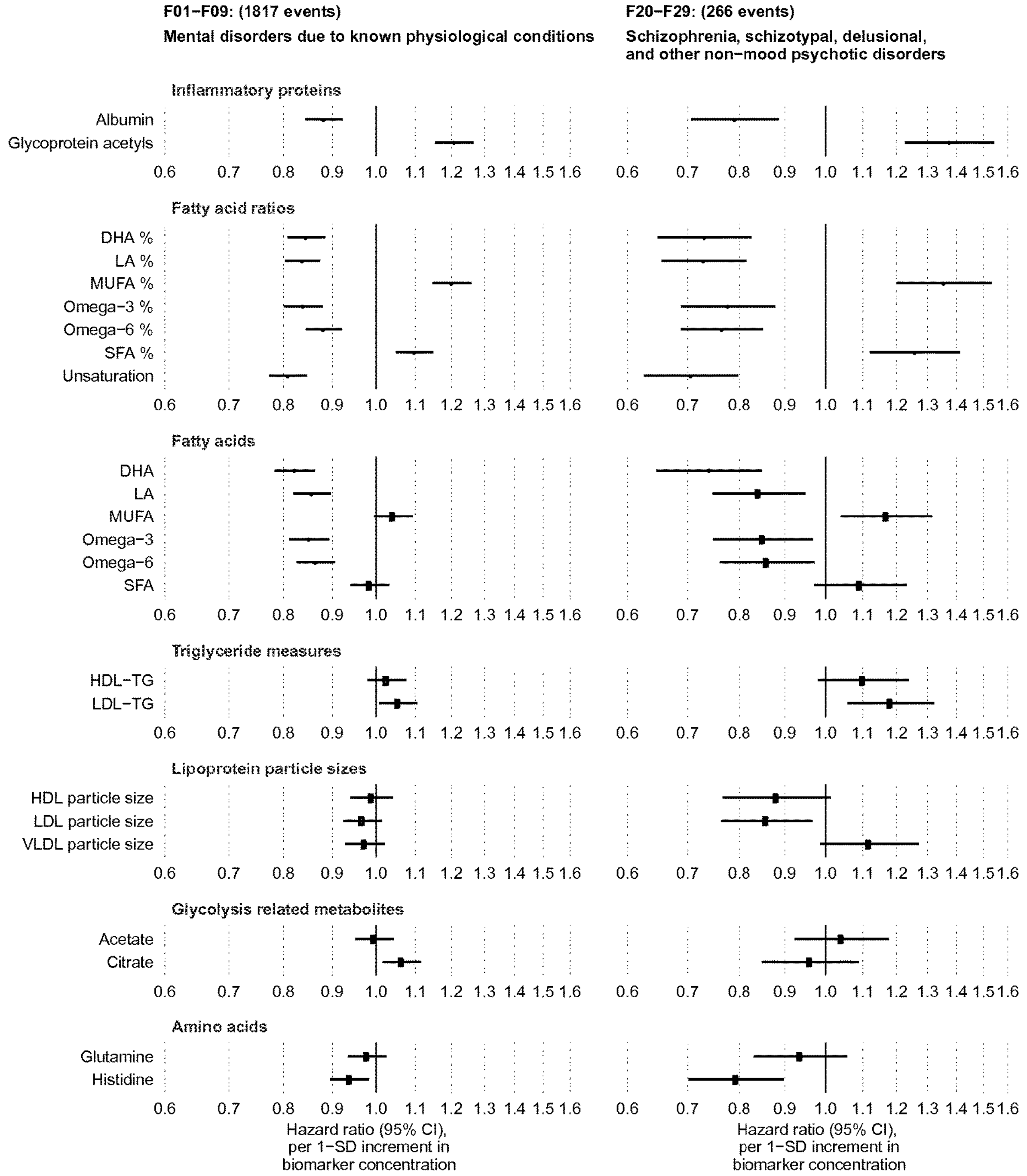
FIGS. 4*a*, 4*b* and 4*c* show the relation of baseline biomarker levels to the future development of 6 different mental and/or behavioural disorder categories (defined by ICD-10 subchapters), in the form of forestplots of the hazard ratios for incident disease onset.
Figure 4B:
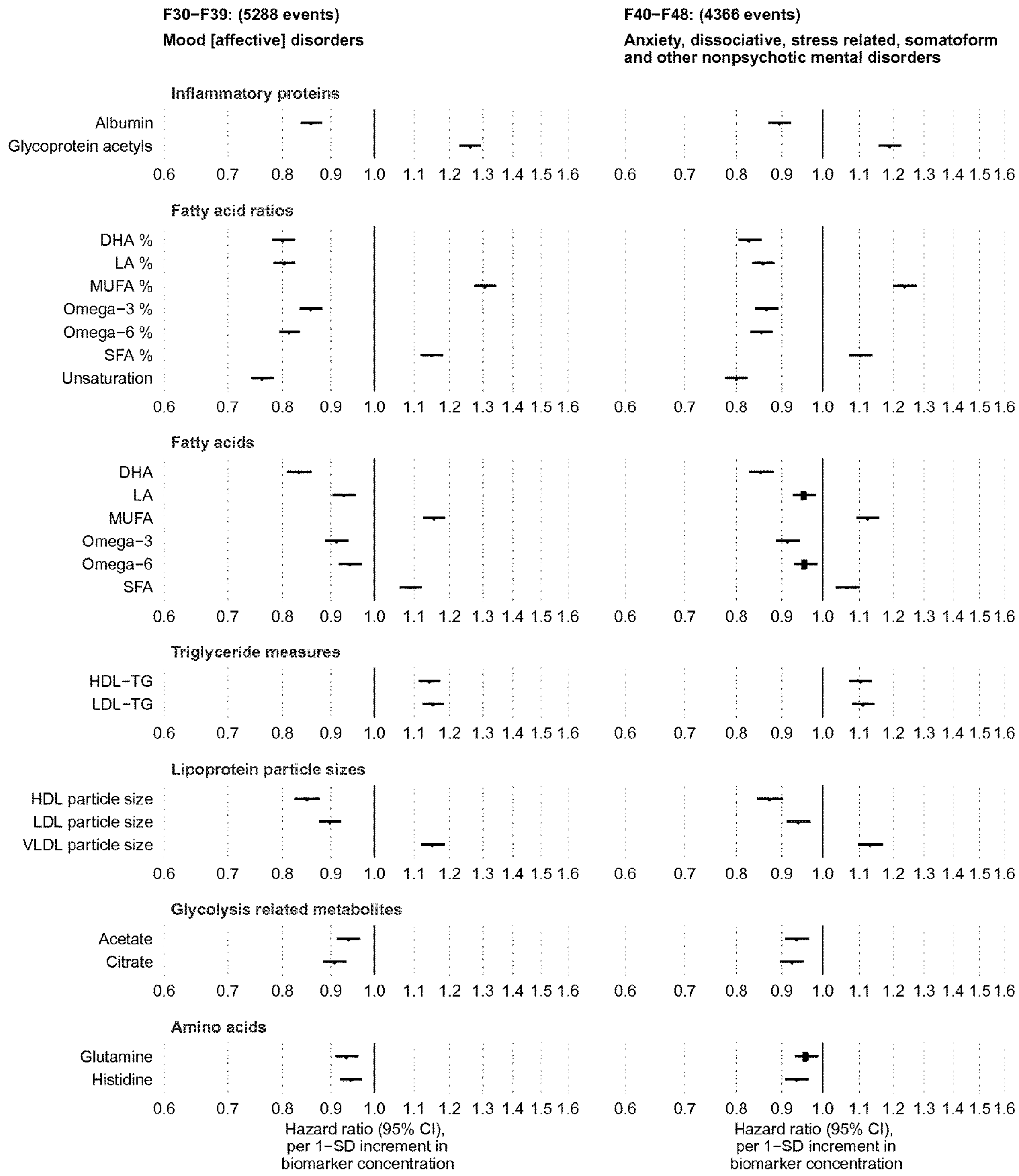
Figure 4C:
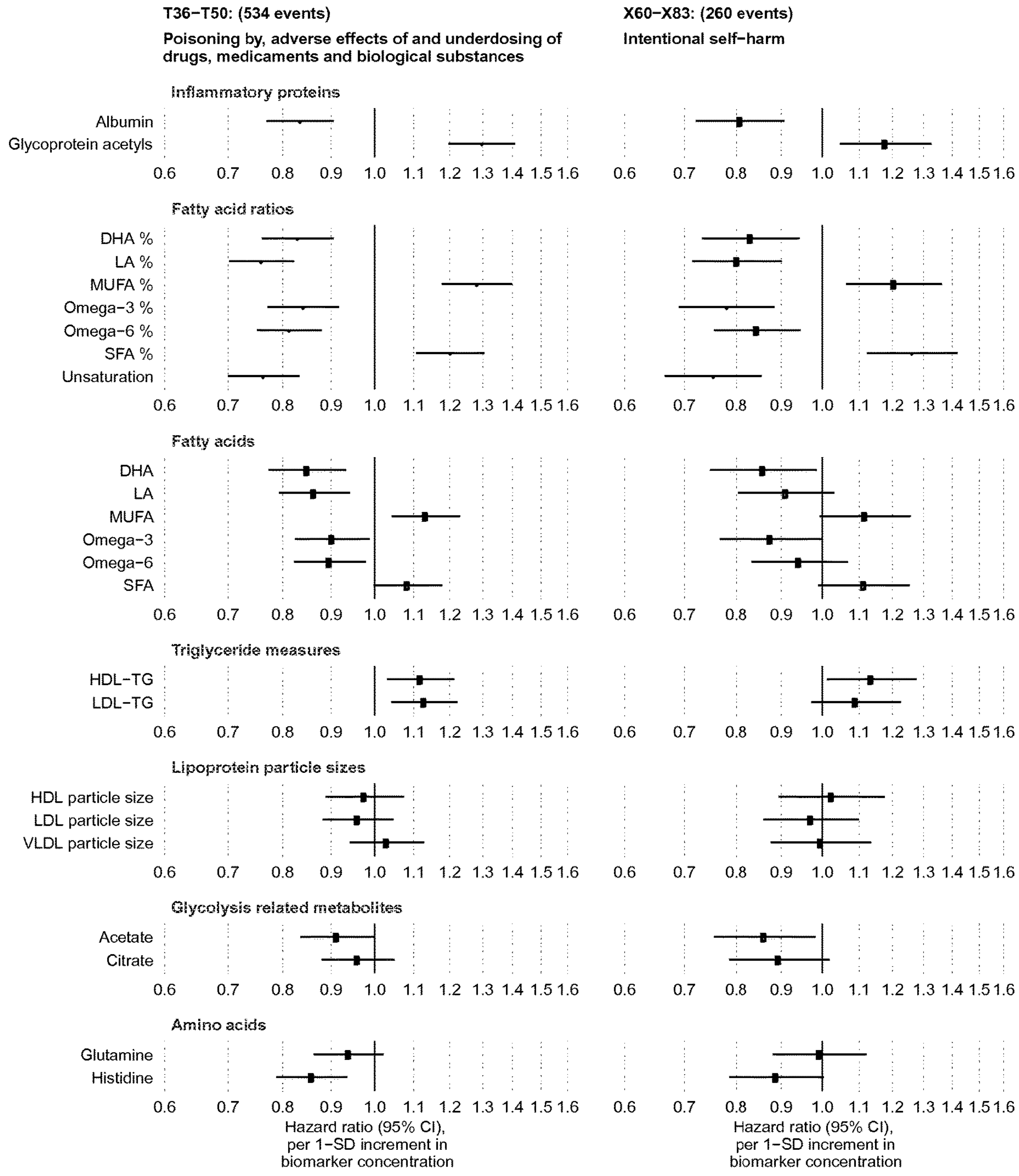
Figure 5A:
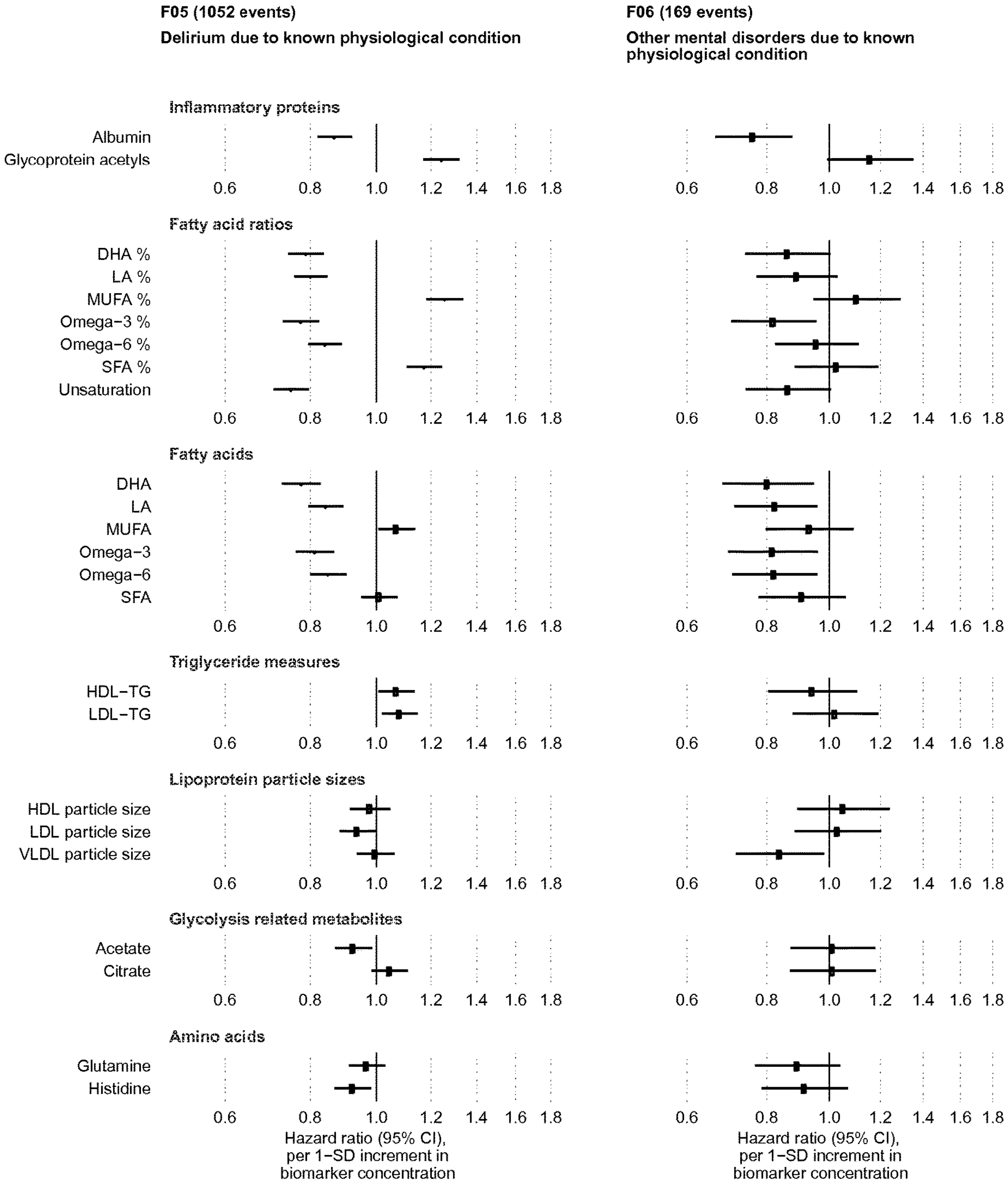
FIGS. 5*a*, 5*b*, 5*c*, 5*d*, 5*e*, 5*f* and 5*g* show the relation of baseline biomarker levels to the future development of 14 specific mental and/or behavioural disorders (defined by ICD-10 3-character diagnoses), in the form of forestplots of the hazard ratios for incident disease onset.
Figure 5B:
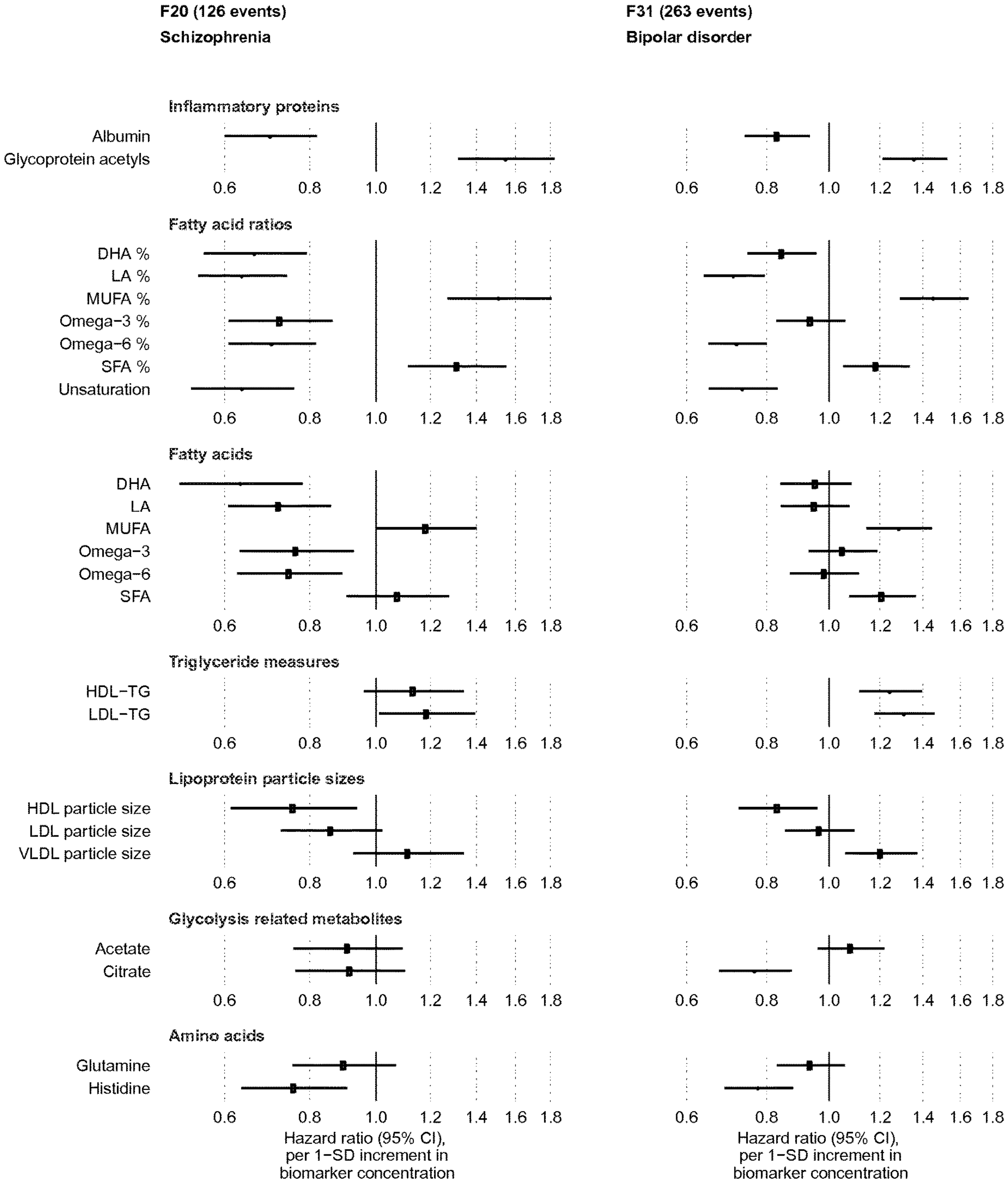
Figure 5C:
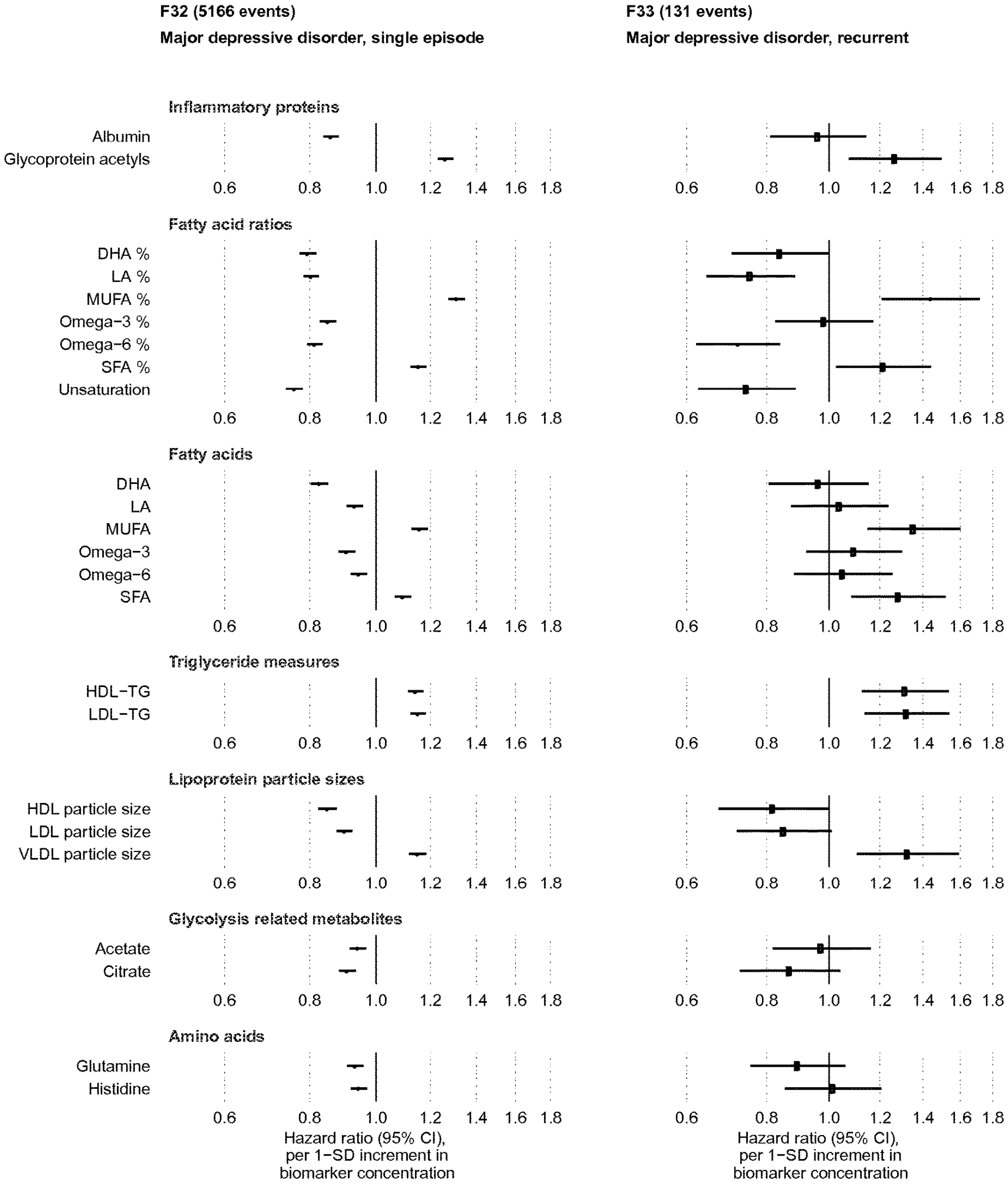
Figure 5D:
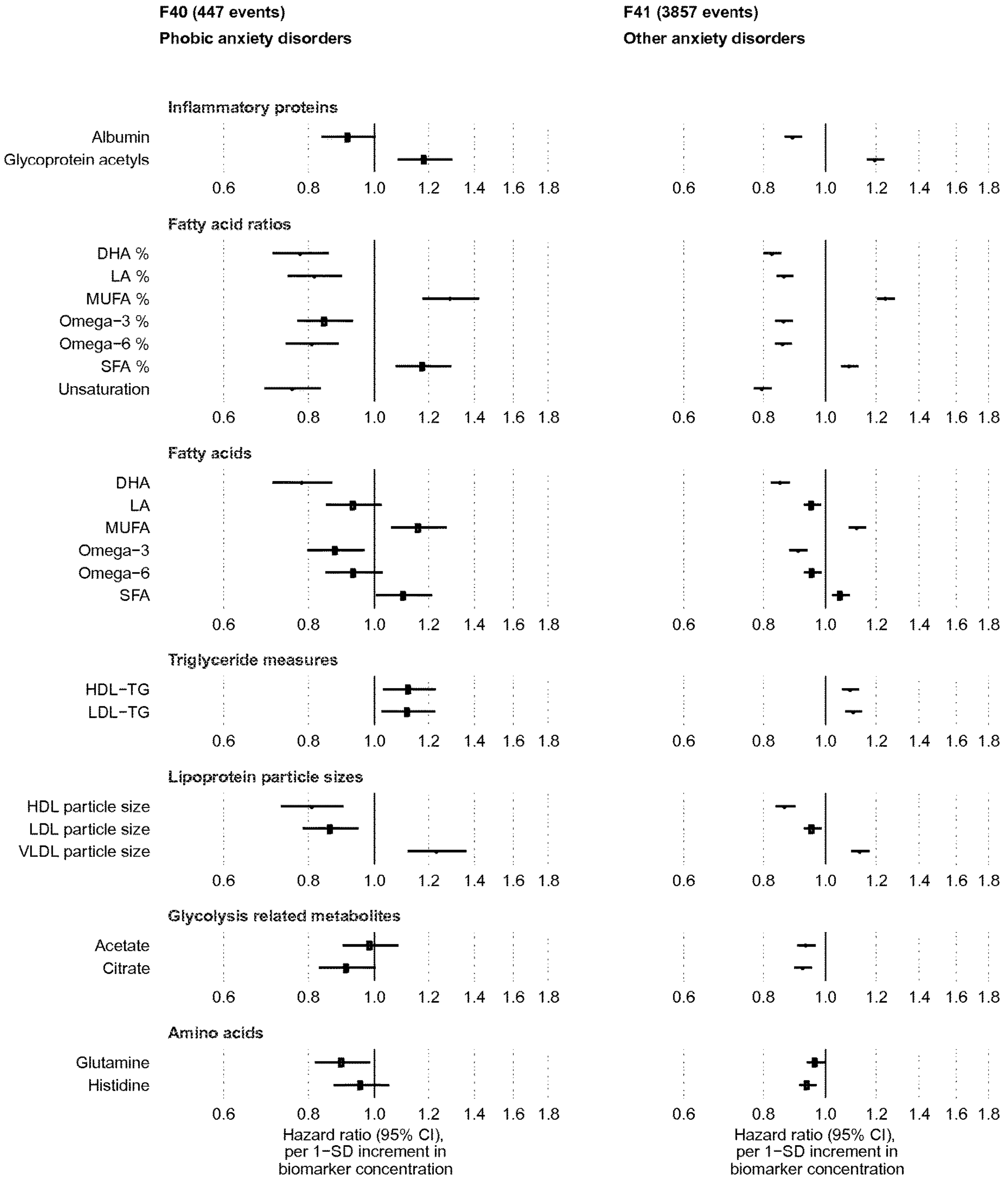
Figure 5E:
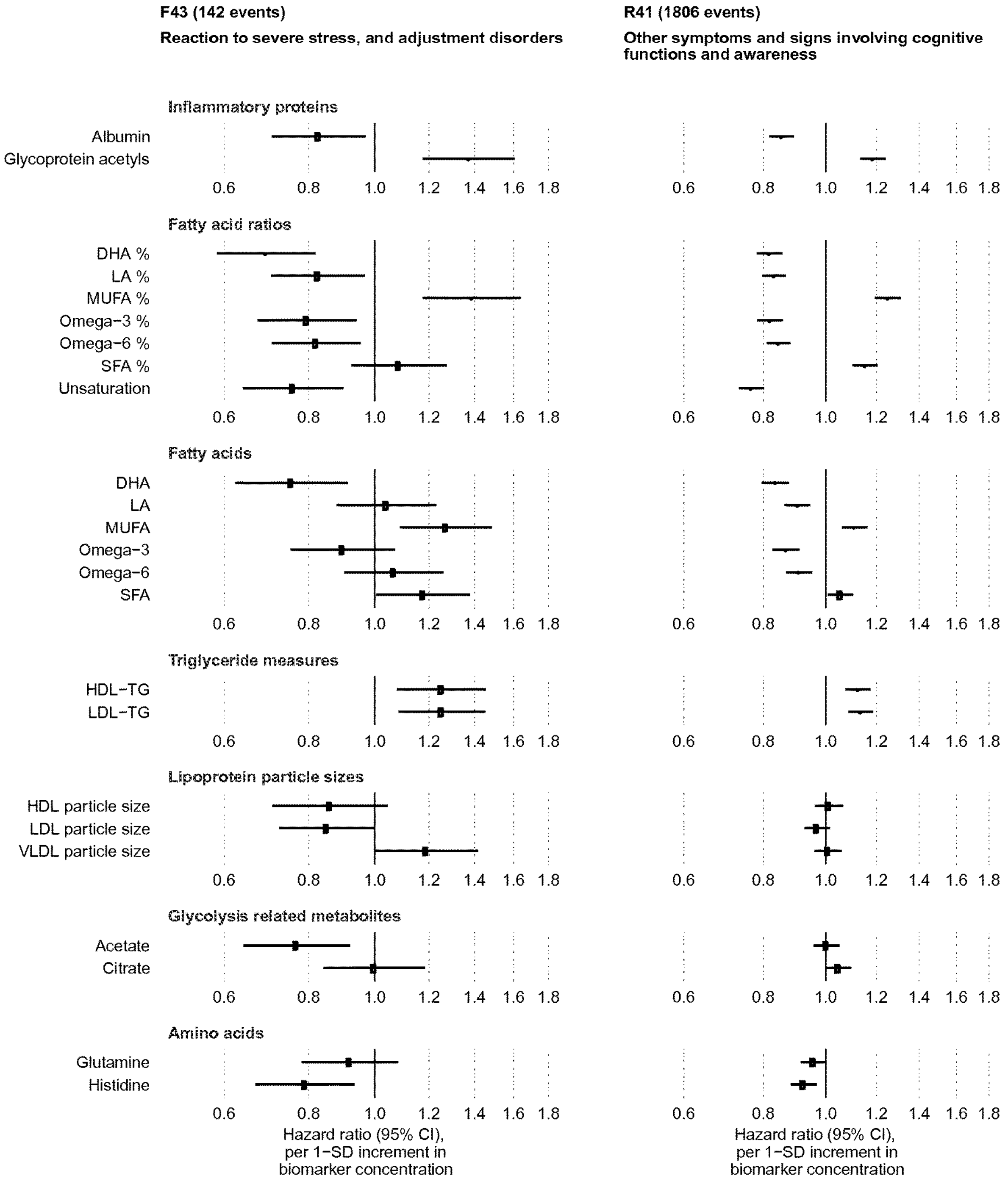
Figure 5F:
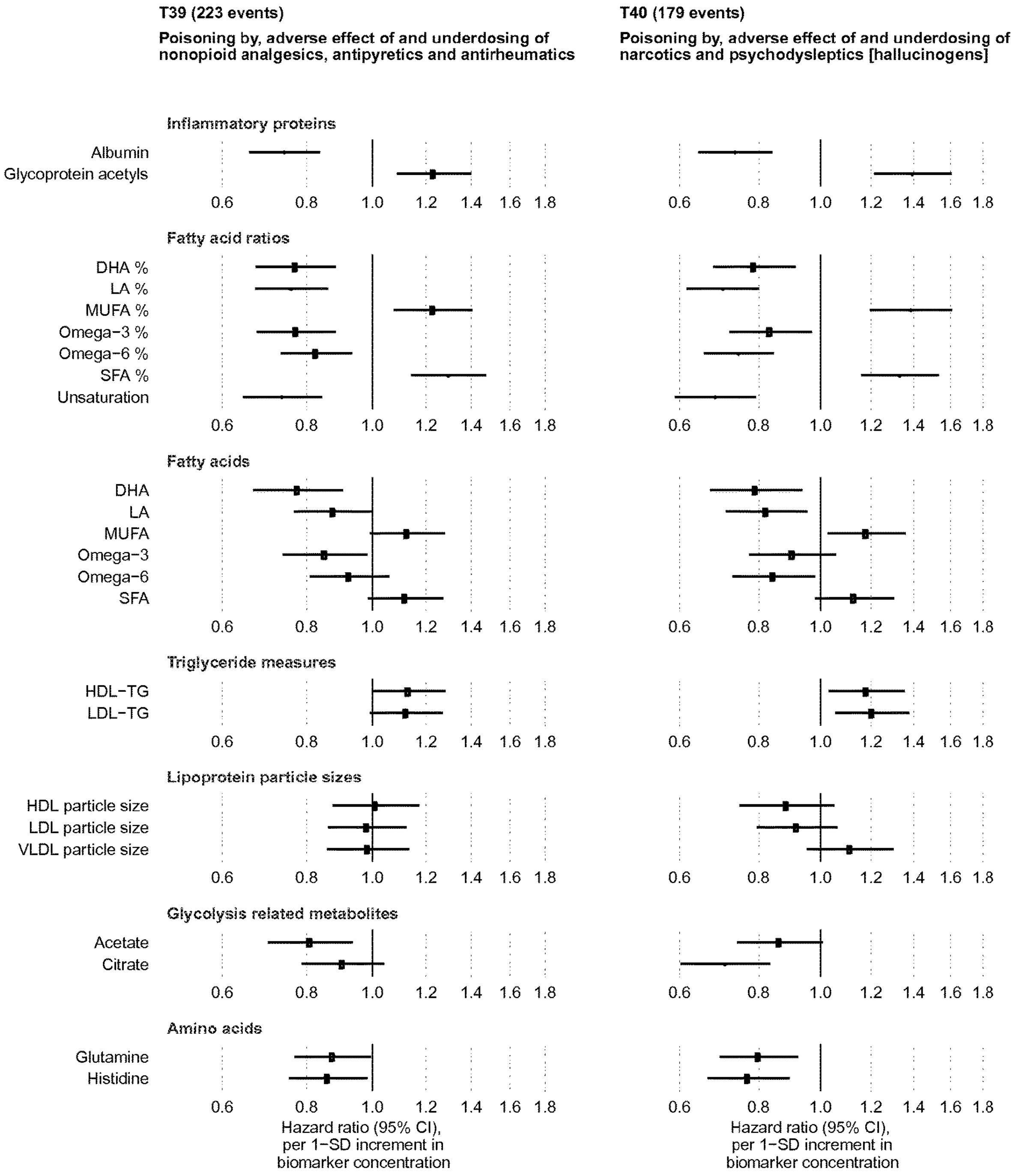
Figure 5G:
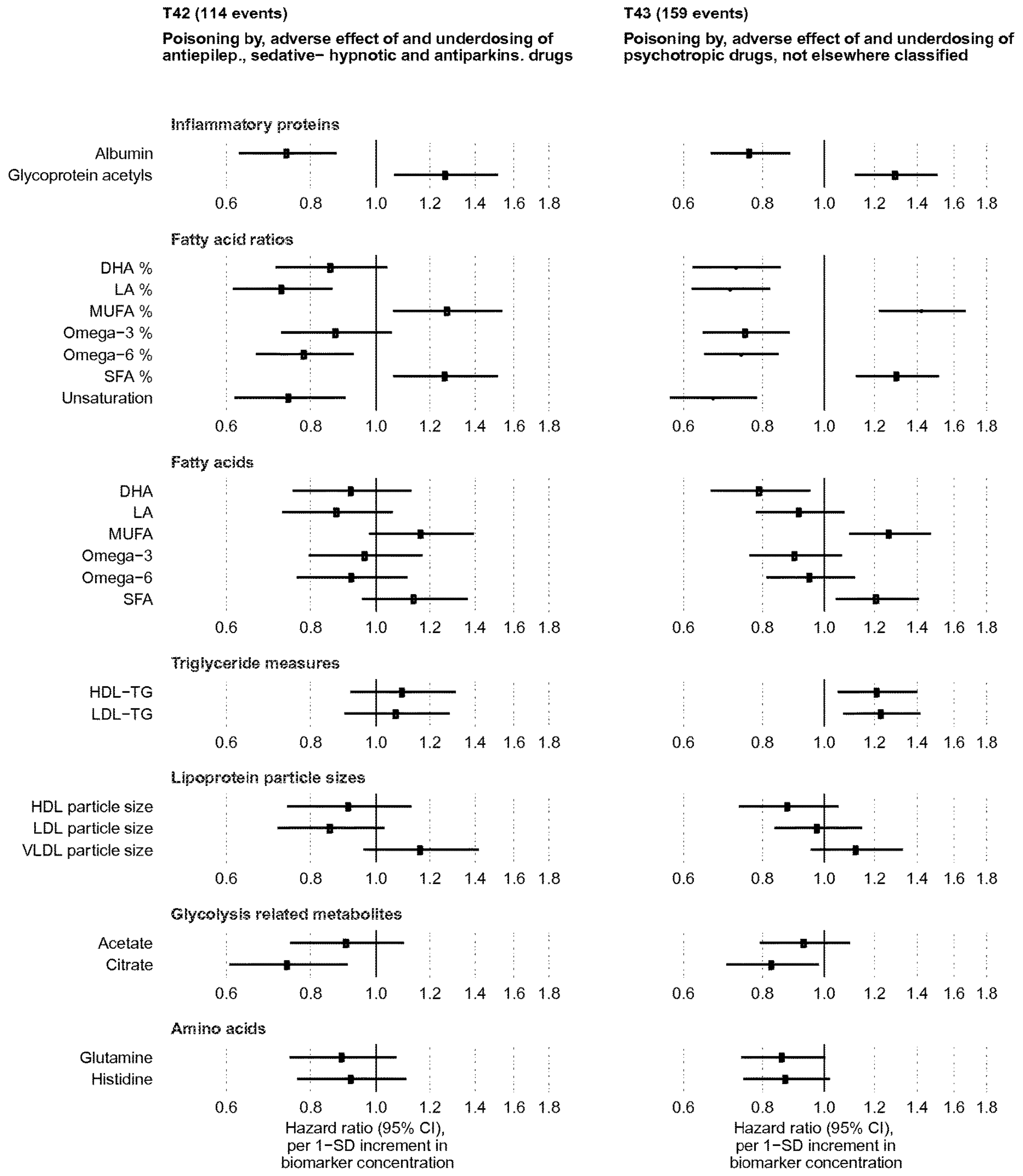

FIGS. 4*a-c* show the hazard ratios for the 24 blood biomarkers with future onset of each of the 6 mental and/or behavioural disorder subgroups (defined by ICD-10 subchapters) studied here. The hazard ratios are shown in absolute concentrations, scaled to the standard deviation of each biomarker. The results are based on statistical analyses of over 115 000 individuals from the UK Biobank; the number of individuals who developed the disorder during approximately 10 years of follow-up is indicated on the top of each plot. Filled circles denote that the P-value for association was P<0.0001 (corresponding to multiple testing correction), and open circles denote that the P-value for association was P≥0.0001. The analyses were adjusted for age, sex, and UK Biobank assessment centre using Cox proportional-hazard regression models.

FIGS. 5*a-g* show the hazard ratios for the 24 blood biomarkers with future onset of each of the 14 specific mental and/or behavioural disorders (defined by ICD-10 3-character diagnosis codes) studied here. The hazard ratios are shown in absolute concentrations, scaled to the standard deviation of each biomarker. The results are based on statistical analyses of over 115 000 individuals from the UK Biobank; the number of individuals who developed the specific disease during approximately 10 years of follow-up is indicated on the top of each plot. Filled circles denote that the P-value for association was P<0.0001 (corresponding to multiple testing correction), and open circles denote that the P-value for association was P≥0.0001. The analyses were adjusted for age, sex, and UK Biobank assessment centre using Cox proportional-hazard regression models.

Figure 6:
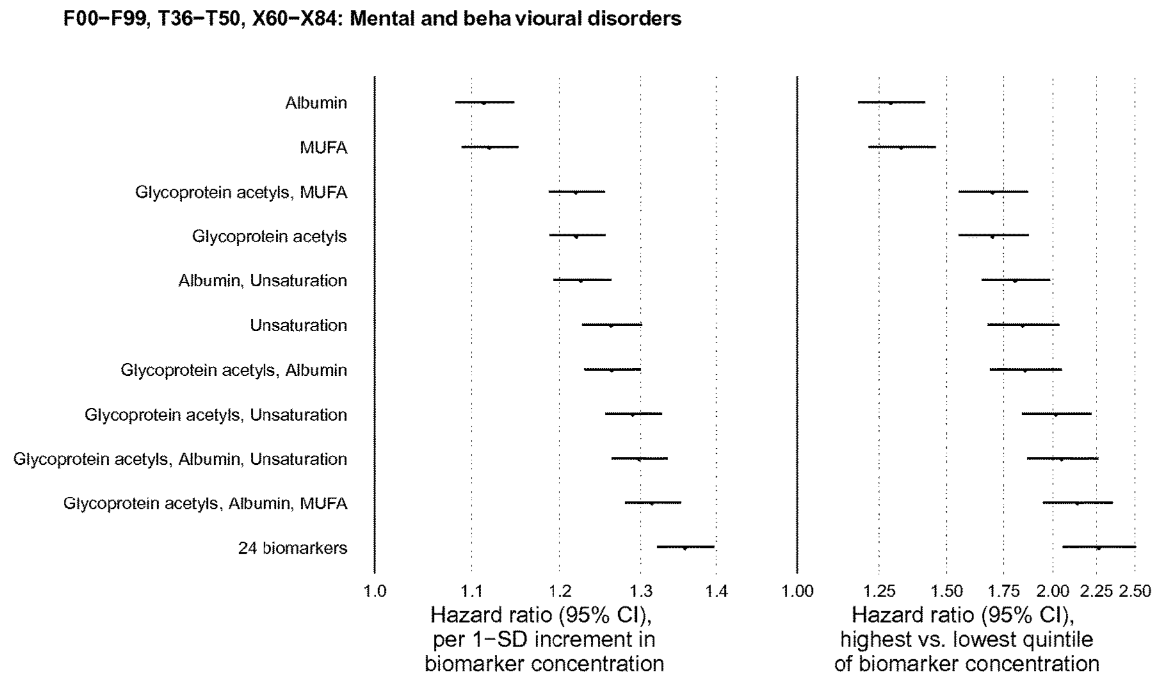
FIG. 6 shows an example of the relation of multi-biomarker scores to the risk of "Any Mental and/or Behavioural Disorder". Selected examples of multi-biomarker scores are shown to illustrate the improved prediction attained by multi-biomarker scores as compared to individual biomarkers.

FIG. 6 shows examples of stronger association results with Any Mental and/or Behavioural Disorder when two or more biomarkers are combined. The hazard ratios with the future risk of Any Mental and/or Behavioural Disorder (composite endpoint of ICD-codes F00-F99, T36-T50 OR X60-X84) are shown for selected combinations of pairs of biomarkers, and examples of biomarker scores. The results were similar with many other combinations, in particular inclusion of different fatty acid measures in addition to albumin and glycoprotein acetyls. The biomarker scores are combined in the form of $\Sigma_i [\![ \beta_i * c_i ]\!] + \beta_0$; where i is the index of summation over individual biomarkers, $\beta_i$ is the weighted coefficient attributed to biomarker i, $c_i$ is the blood concentration of biomarker i and $\beta_0$ is an intercept term. $\beta_i$ multipliers are defined according to the multivariate association magnitude with the risk for Any Mental and/or Behavioural Disorder, examined in the statistical analyses of the UK Biobank study for the respective combination of biomarkers. The enhancements in association magnitudes were similar for the 14 specific types of mental and/or behavioural disorders listed in Table 1 as those shown here for Any Mental and/or Behavioural Disorder.

Illustrations of Intended Use: Biomarker Scores for Risk Prediction of a Mental and/or a Behavioural Disorder For illustration of intended applications related to the prediction of a mental and/or a behavioural disorder, further epidemiological analyses are illustrated below. These applications are exemplified for the prediction of the risk for mood affective disorders, anxiety, dissociative, stress-related, somatoform and other nonpsychotic disorders, delirium, major depressive disorder, anxiety disorders and other symptoms and signs involving cognitive functions and awareness. Similar results apply to the other mental and/or behavioural disorders listed in Table 1. Results are shown for a biomarker score combining the 24 biomarkers featured in FIGS. 1-6. Similar results, albeit slightly weaker, are obtained with combinations of only two or three individual biomarkers.

Figure 7A:
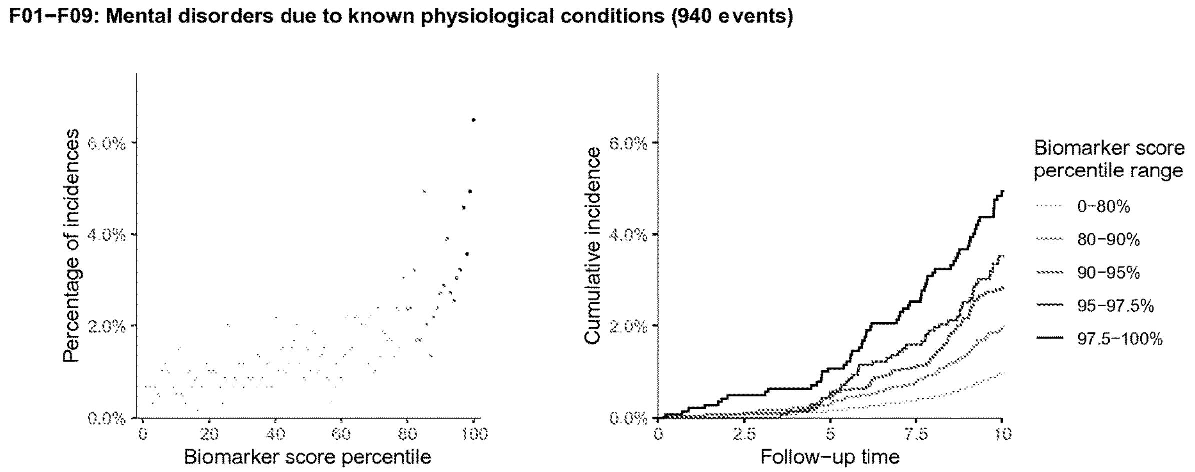
FIG. 7*a* shows an intended use case for a multi-biomarker score to predict the risk for developing mental disorders due to known physiological conditions among initially healthy humans.

FIG. 7*a* shows the increase in the risk for mental disorders due to known physiological conditions (ICD-10 subchapter F01-F09) along with increasing levels of a multi-biomarker score composed of the weighted sum of 24 biomarkers. On the left-hand side, the risk increase is plotted in the form of gradient percentile plots, showing the proportion of individuals who developed mental disorders due to known physiological conditions during follow-up when binning individuals into the percentiles of the biomarker score levels. Each dot corresponds to approximately 500 individuals. In the Kaplan-Meier plots on the right-hand side, the cumulative risk for mental disorders due to known physiological conditions during follow-up is illustrated for selected quantiles of the multi-biomarker score. Both plots serve to demonstrate that the risk is increasing non-linearly in the high end of the distribution of the multi-biomarker score. The plots are shown for the validation set part of the study population, i.e. 50% which was not included for derivation of the multi-biomarker score (n=58 751 individuals).

Figure 7B:
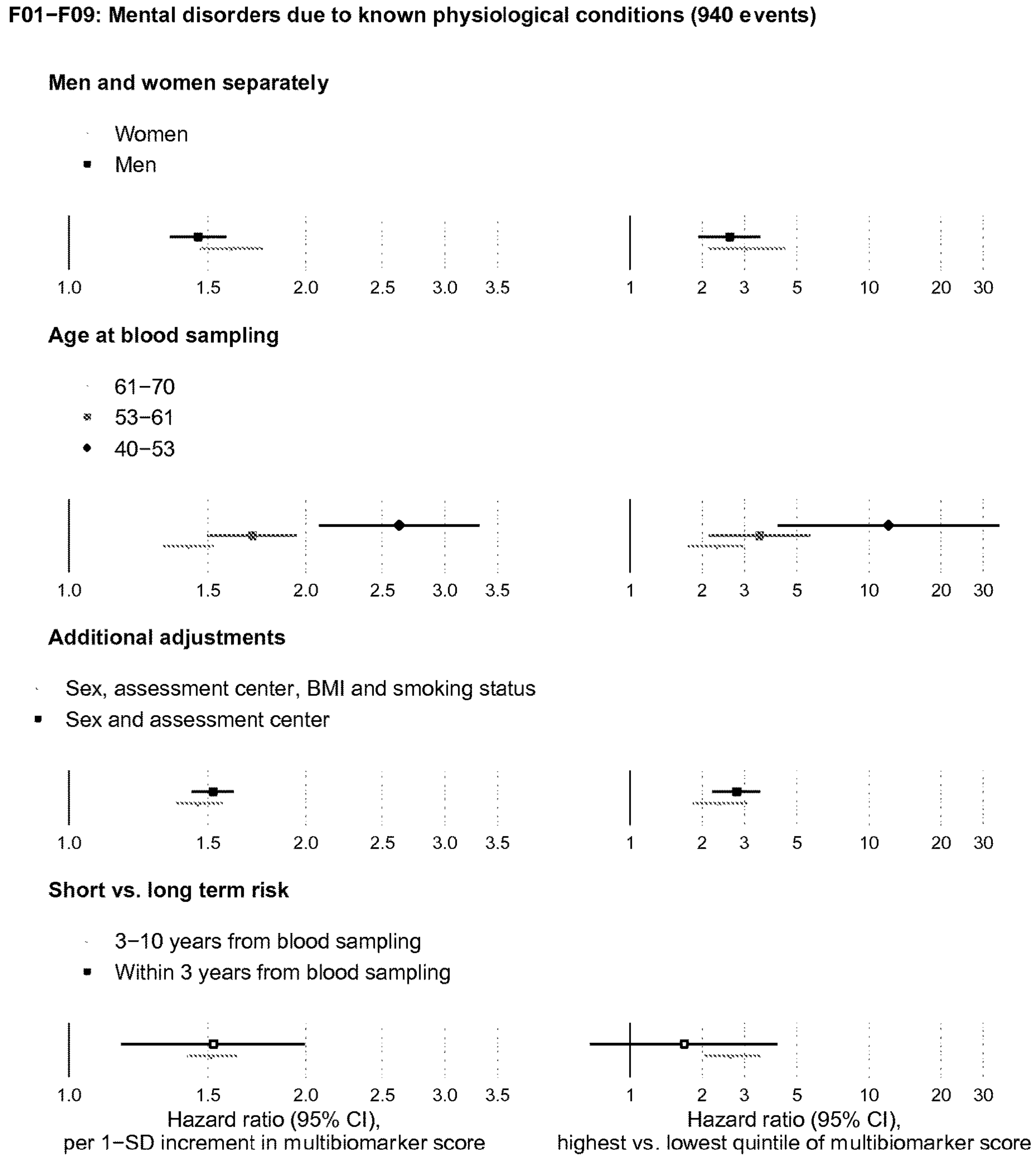
FIG. 7*b* shows that the prediction of the risk for developing mental disorders due to known physiological conditions works effectively for people with different demographics and risk factor profiles.

FIG. 7*b* shows the hazard ratio of the same multi-biomarker score with the future onset of mental disorders due to known physiological conditions (ICD-10 subchapter F01-F09) when accounting for relevant risk factor characteristics of the study participants. The first panel demonstrates that the risk prediction works effectively for both men and women. The second panel shows that risk prediction also works for people at different ages at the time of blood sampling, with stronger results for younger individuals. The third panel shows that the magnitude of the hazard ratio is only modestly attenuated when accounting for body mass index and smoking status in the statistical modelling. The last panel demontrates that the hazard ratios are similar for both short and long term risk prediction.

Figure 8A:
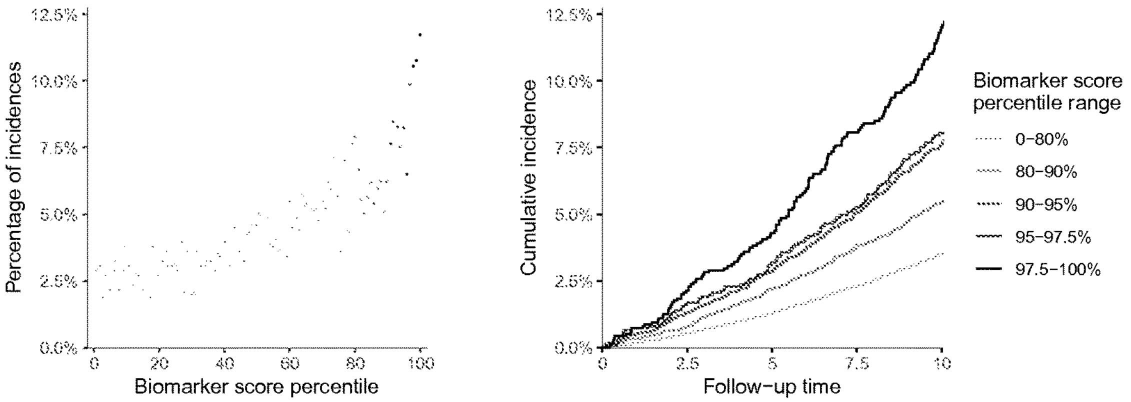
FIG. 8*a* shows an intended use case for a multi-biomarker score to predict the risk for developing mood affective disorders among initially healthy humans.

FIG. 8*a* shows the increase in the risk for mood affective disorders (ICD-10 subchapter F30-F39) along with increasing levels of a multi-biomarker score composed of the weighted sum of 24 biomarkers. On the left-hand side, the risk increase is plotted in the form of gradient percentile plots, showing the proportion of individuals who developed mood affective disorders during follow-up when binning individuals into the percentiles of the biomarker score levels. Each dot corresponds to approximately 500 individuals. In the Kaplan-Meier plots on the right-hand side, the cumulative risk for mood affective disorders during follow-up is illustrated for selected quantiles of the multi-biomarker score. Both plots serve to demonstrate that the risk is increasing non-linearly in the high end of the distribution of the multi-biomarker score. The plots are shown for the validation set part of the study population, i.e. 50% which was not included for derivation of the multi-biomarker score (n=57 643 individuals).

Figure 8B:
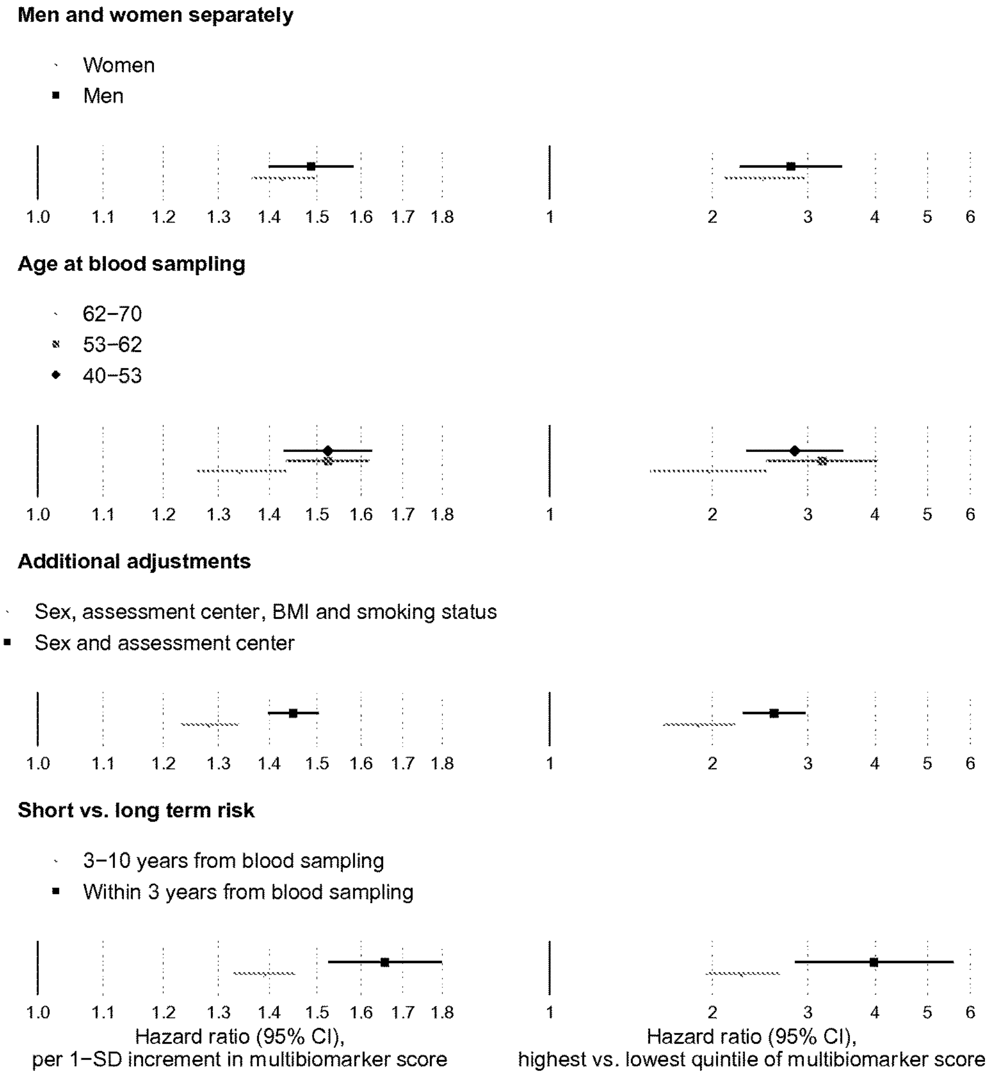
FIG. 8*b* shows that the prediction of the risk for developing mood affective disorders works effectively for people with different demographics and risk factor profiles.

FIG. 8*b* shows the hazard ratio of the same multi-biomarker score with the future onset of mood affective disorders (ICD-10 subchapter F30-F39) when accounting for relevant risk factor characteristics of the study participants. The first and the second panel demonstrate that the risk prediction works effectively for both men and women, and for people at different ages at the time of blood sampling. The third panel shows that the magnitude of the hazard ratio is only modestly attenuated when accounting for body mass index and smoking status in the statistical modelling. The last panel demonstrates that the hazard ratio is substantially stronger when focusing on short-term risk prediction.

Figure 9A:
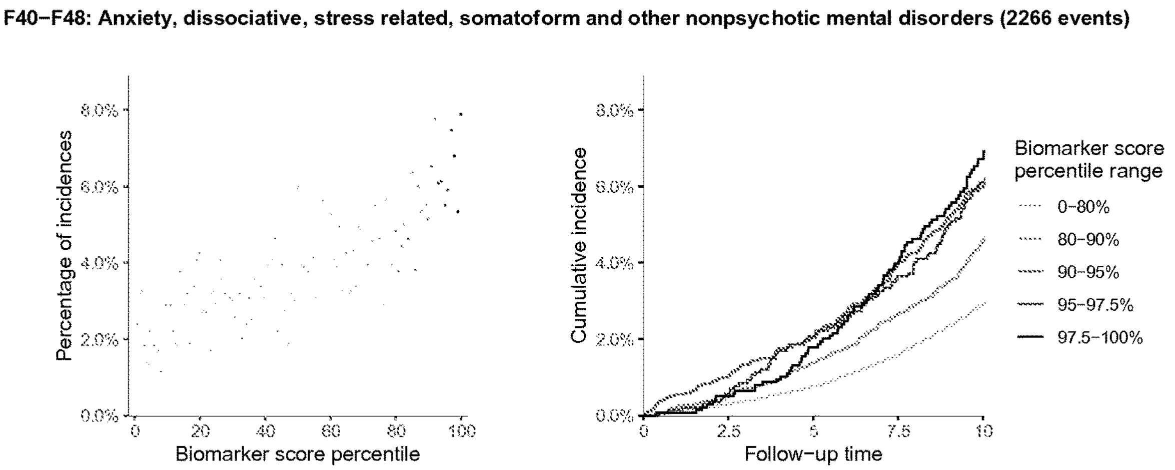
FIG. 9*a* shows an intended use case for a multi-biomarker score to predict the risk for developing anxiety, dissociative, stress related, somatoform and other nonpsychotic mental disorders among initially healthy humans.

FIG. 9*a* shows the increase in the risk for anxiety, dissociative, stress related, somatoform and other nonpsychotic mental disorders (ICD-10 subchapter F40-F48) along with increasing levels of a multi-biomarker score composed of the weighted sum of 24 biomarkers. On the left-hand side, the risk increase is plotted in the form of gradient percentile plots, showing the proportion of individuals who developed anxiety, dissociative, stress related, somatoform and other nonpsychotic mental disorders during follow-up when binning individuals into the percentiles of the biomarker score levels. Each dot corresponds to approximately 500 individuals. In the Kaplan-Meier plots on the right-hand side, the cumulative risk for anxiety, dissociative, stress related, somatoform and other nonpsychotic mental disorders during follow-up is illustrated for selected quantiles of the multi-biomarker score. Both plots serve to demonstrate that the risk is increasing non-linearly in the high end of the distribution of the multi-biomarker score. The plots are shown for the validation set part of the study population, i.e. 50% which was not included for derivation of the multi-biomarker score (n=58 236 individuals).

Figure 9B:
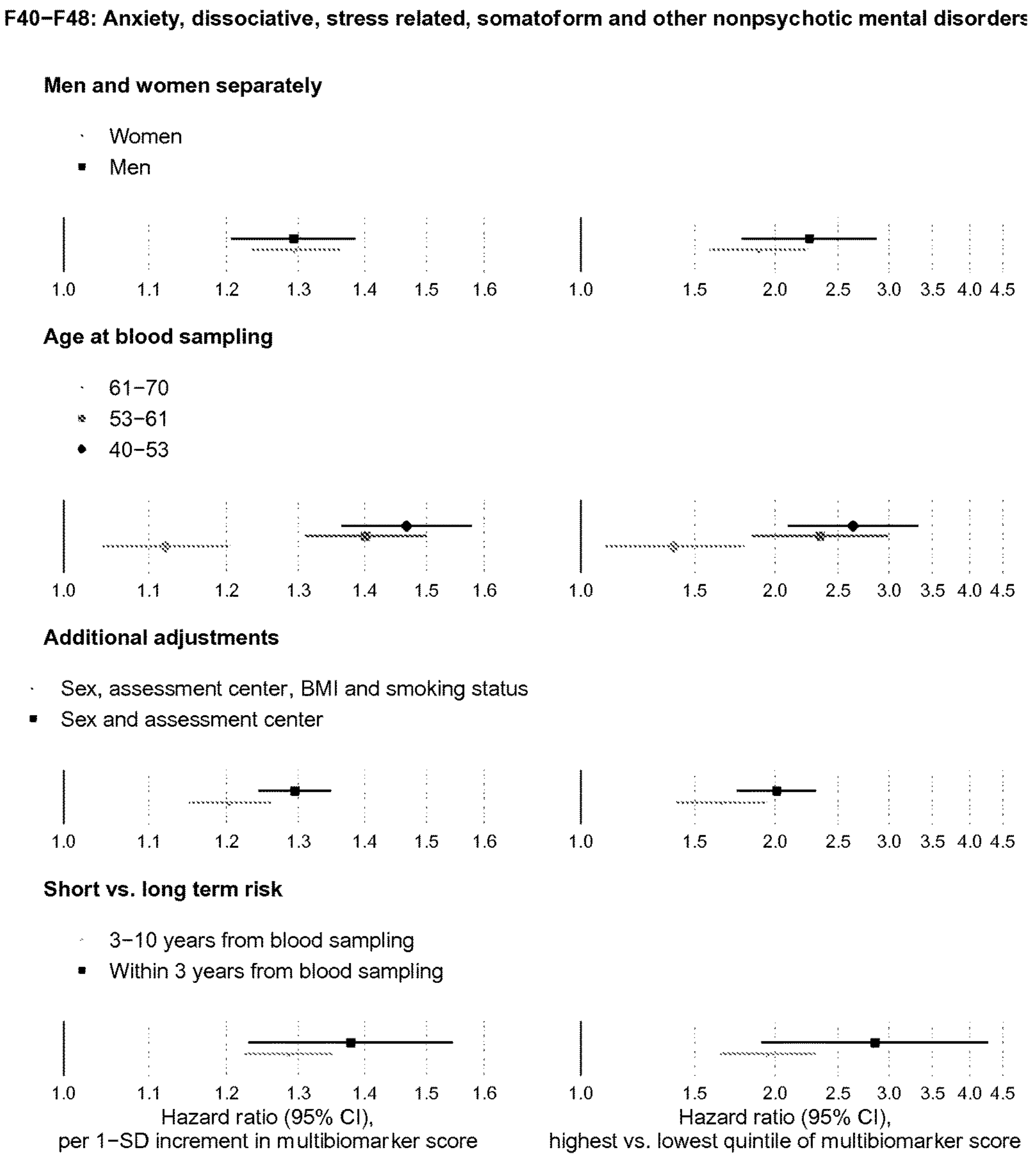
FIG. 9*b* shows that the prediction of the risk for anxiety, dissociative, stress related, somatoform and other nonpsychotic mental disorders works effectively for people with different demographics and risk factor profiles.

FIG. 9*b* shows the hazard ratio of the same multi-biomarker score with the future onset of anxiety, dissociative, stress related, somatoform and other nonpsychotic mental disorders (ICD-10 subchapter F40-F48) when accounting for relevant risk factor characteristics of the study participants. The first two panels demonstrate that the risk prediction works effectively for both men and women, and for people at different ages at the time of blood sampling, with stronger results for younger individuals. The third panel shows that the magnitude of the hazard ratio is only modestly attenuated when accounting for body mass index and smoking status in the statistical modelling. The last panel demonstrates that the hazard ratio is substantially stronger when focusing on short-term risk prediction.

Figure 10A:
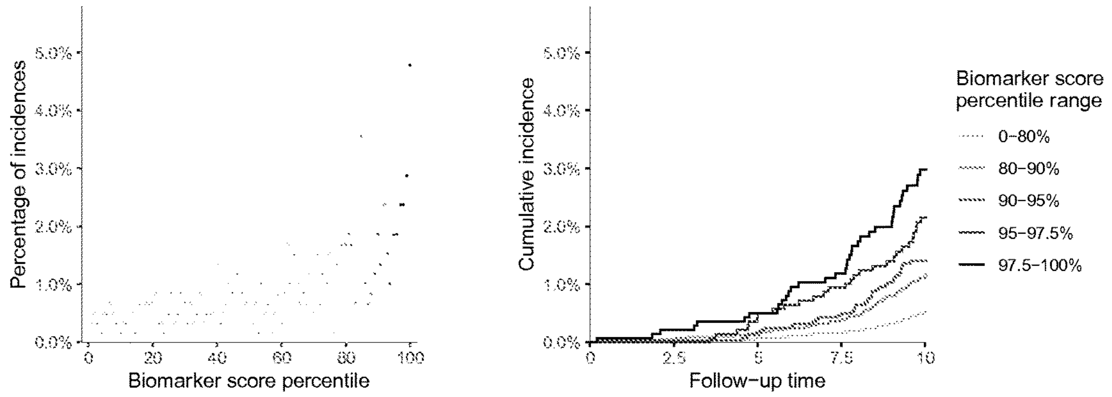
FIG. 10*a* shows an intended use case for a multi-biomarker score to predict the risk for developing delirium due to known physiological condition among initially healthy humans.

FIG. 10*a* shows the increase in the risk for delirium due to known physiological condition (ICD-10 code F05) along with increasing levels of a multi-biomarker score composed of the weighted sum of 24 biomarkers. On the left-hand side, the risk increase is plotted in the form of gradient percentile plots, showing the proportion of individuals who developed delirium due to known physiological condition during follow-up when binning individuals into the percentiles of the biomarker score levels. Each dot corresponds to approximately 500 individuals. In the Kaplan-Meier plots on the right-hand side, the cumulative risk for delirium due to known physiological condition during follow-up is illustrated for selected quantiles of the multi-biomarker score. Both plots serve to demonstrate that the risk is increasing non-linearly in the high end of the distribution of the multi-biomarker score. The plots are shown for the validation set part of the study population, i.e. 50% which was not included for derivation of the multi-biomarker score (n=58 793 individuals).

Figure 10B:
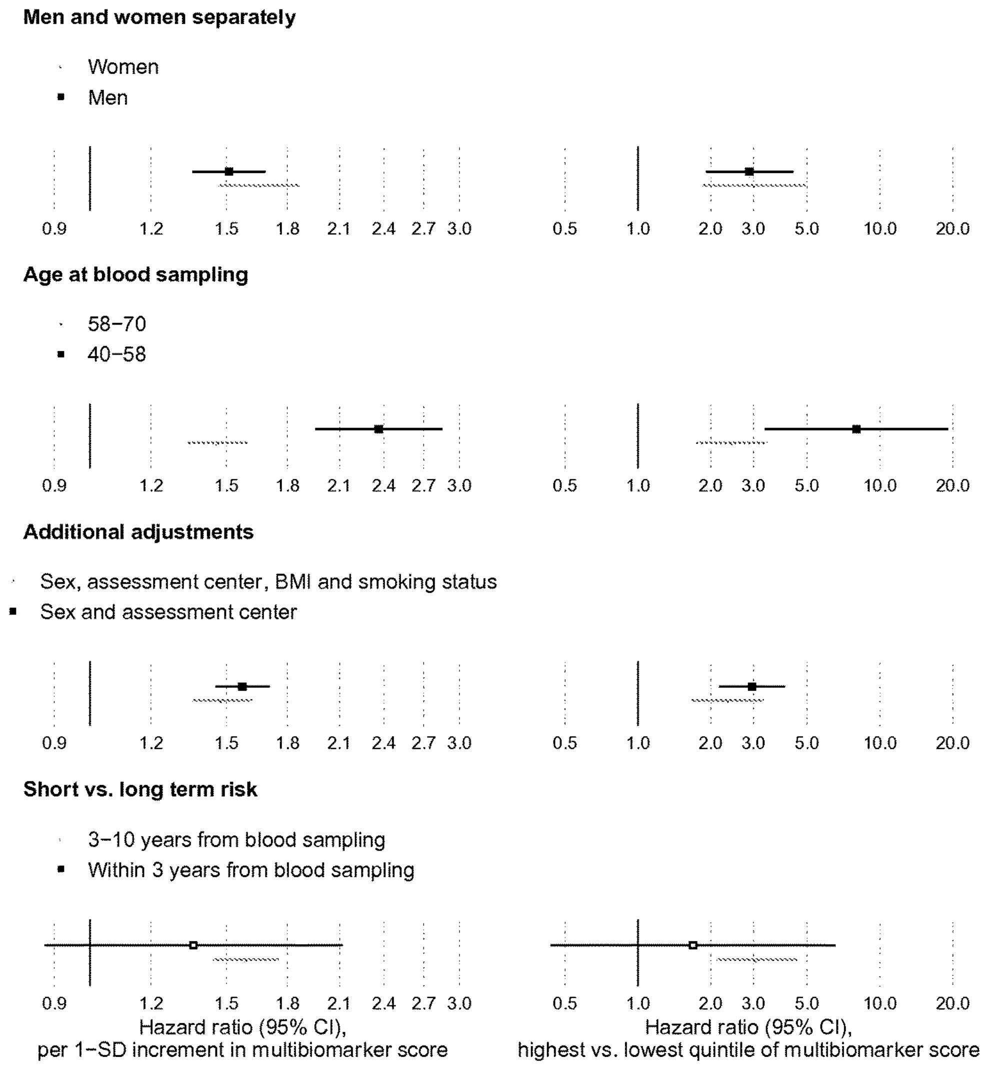
FIG. 10*b* shows that the prediction of the risk for developing delirium due to known physiological condition works effectively for people with different demographics and risk factor profiles.

FIG. 10*b* shows the hazard ratio of the same multi-biomarker score with the future onset of delirium due to known physiological condition (ICD-10 code F05) when accounting for relevant risk factor characteristics of the study participants. The first panel demonstrates that the risk prediction works effectively for both men and women. The second panel shows that risk prediction also works for people at different ages at the time of blood sampling, with stronger results for younger individuals. The third panel shows that the magnitude of the hazard ratio is only modestly attenuated when accounting for body mass index and smoking status in the statistical modelling. The last panel demontrates that the hazard ratio is substantially stronger when focusing on short-term risk prediction.

Figure 11A:
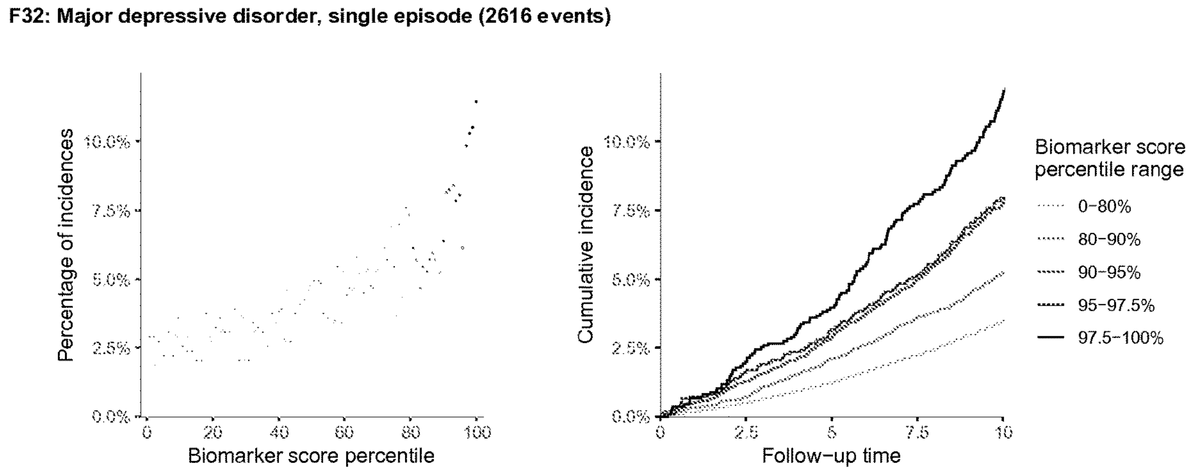
FIG. 11*a* shows an intended use case for a multi-biomarker score to predict the risk for developing major depressive disorder, single episode among initially healthy humans.

FIG. 11*a* shows the increase in the risk for major depressive disorder, single episode (ICD-10 code F32) along with increasing levels of a multi-biomarker score composed of the weighted sum of 24 biomarkers. On the left-hand side, the risk increase is plotted in the form of gradient percentile plots, showing the proportion of individuals who developed major depressive disorder, single episode during follow-up when binning individuals into the percentiles of the biomarker score levels. Each dot corresponds to approximately 500 individuals. In the Kaplan-Meier plots on the right-hand side, the cumulative risk for major depressive disorder, single episode during follow-up is illustrated for selected quantiles of the multi-biomarker score. Both plots serve to demonstrate that the risk is increasing non-linearly in the high end of the distribution of the multi-biomarker score. The plots are shown for the validation set part of the study population, i.e. 50% which was not included for derivation of the multi-biomarker score (n=57 822 individuals).

Figure 11B:
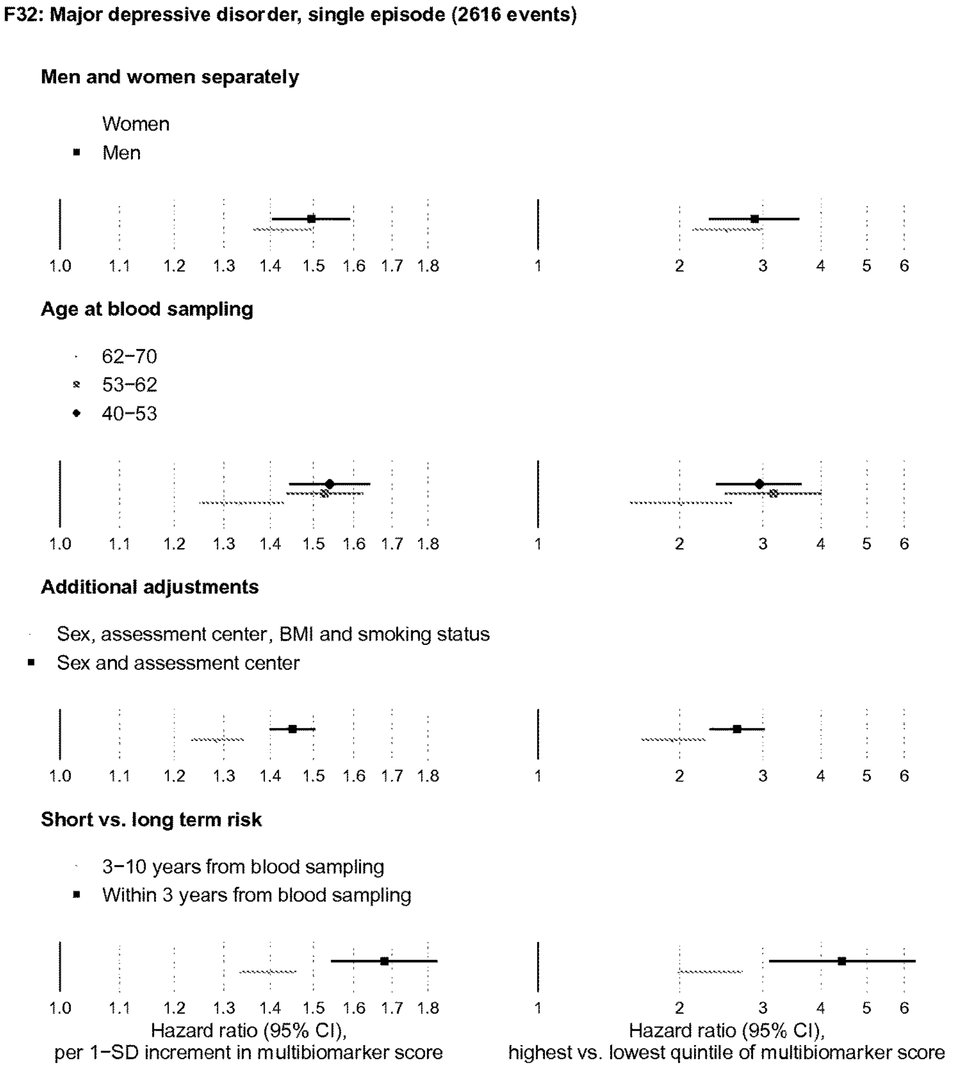
FIG. 11*b* shows that the prediction of the risk for developing major depressive disorder, single episode works effectively for people with different demographics and risk factor profiles.

FIG. 11*b* shows the hazard ratio of the same multi-biomarker score with the future onset of major depressive disorder, single episode (ICD-10 code F32) when accounting for relevant risk factor characteristics of the study participants. The first two panels demonstrate that the risk prediction works effectively for both men and women, and for people at different ages at the time of blood sampling. The third panel shows that the magnitude of the hazard ratio is only modestly attenuated when accounting for body mass index and smoking status in the statistical modelling. The last panel demontrates that the hazard ratio is substantially stronger when focusing on short-term risk prediction.

Figure 12A:
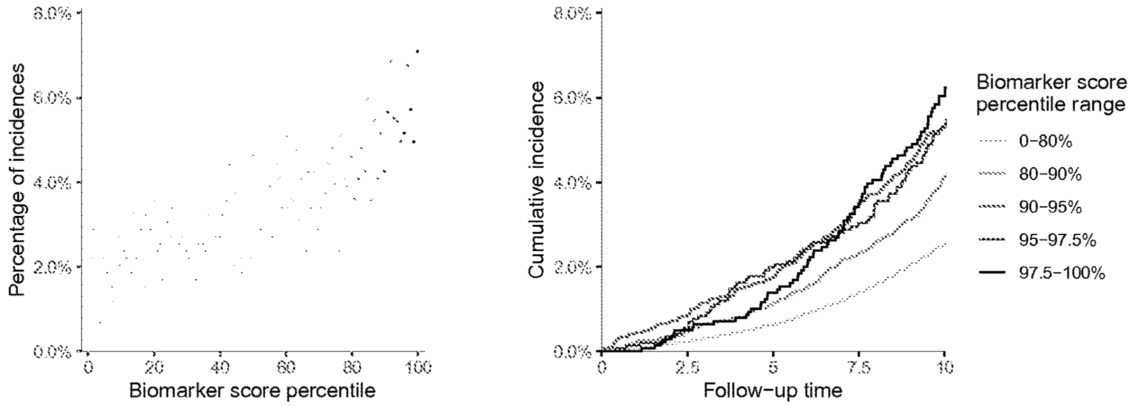
FIG. 12*a* shows an intended use case for a multi-biomarker score to predict the risk for developing anxiety disorders among initially healthy humans.

FIG. 12*a* shows the increase in the risk for anxiety disorders (ICD-10 code F41) along with increasing levels of a multi-biomarker score composed of the weighted sum of 24 biomarkers. On the left-hand side, the risk increase is plotted in the form of gradient percentile plots, showing the proportion of individuals who developed anxiety disorders during follow-up when binning individuals into the percentiles of the biomarker score levels. Each dot corresponds to approximately 500 individuals. In the Kaplan-Meier plots on the right-hand side, the cumulative risk for anxiety disorders during follow-up is illustrated for selected quantiles of the multi-biomarker score. Both plots serve to demonstrate that the risk is increasing non-linearly in the high end of the distribution of the multi-biomarker score. The plots are shown for the validation set part of the study population, i.e. 50% which was not included for derivation of the multi-biomarker score (n=58 451 individuals).

Figure 12B:
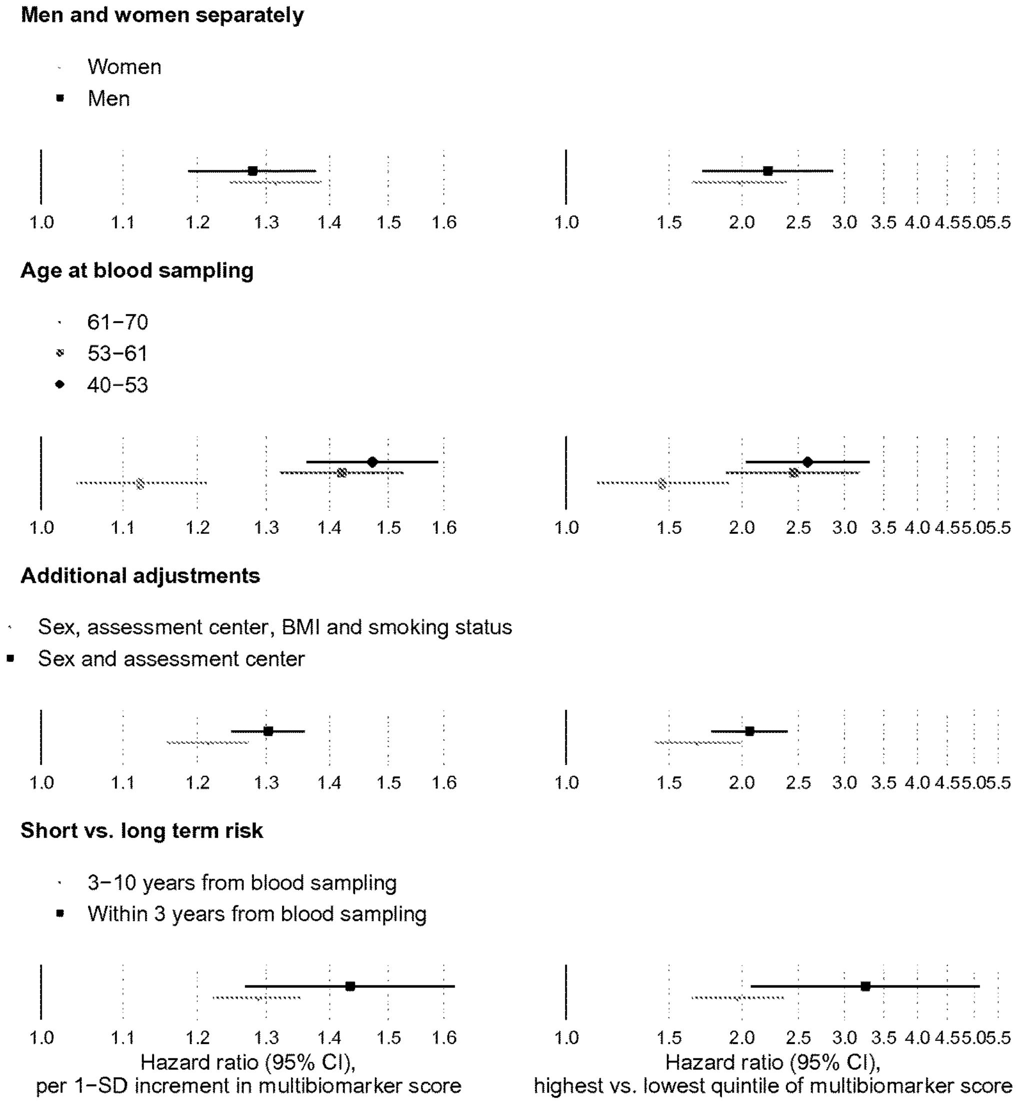
FIG. 12*b* shows that the prediction of the risk for developing anxiety disorders works effectively for people with different demographics and risk factor profiles.

FIG. 12*b* shows the hazard ratio of the same multi-biomarker score with the future onset of anxiety disorders (ICD-10 code F41) when accounting for relevant risk factor characteristics of the study participants. The first panel demonstrates that the risk prediction works effectively for both men and women. The second panel shows that risk prediction also works for people at different ages at the time of blood sampling, with stronger results for younger individuals. The third panel shows that the magnitude of the hazard ratio is only modestly attenuated when accounting for body mass index and smoking status in the statistical modelling. The last panel demontrates that the hazard ratio is substantially stronger when focusing on short-term risk prediction.

Figure 13A:
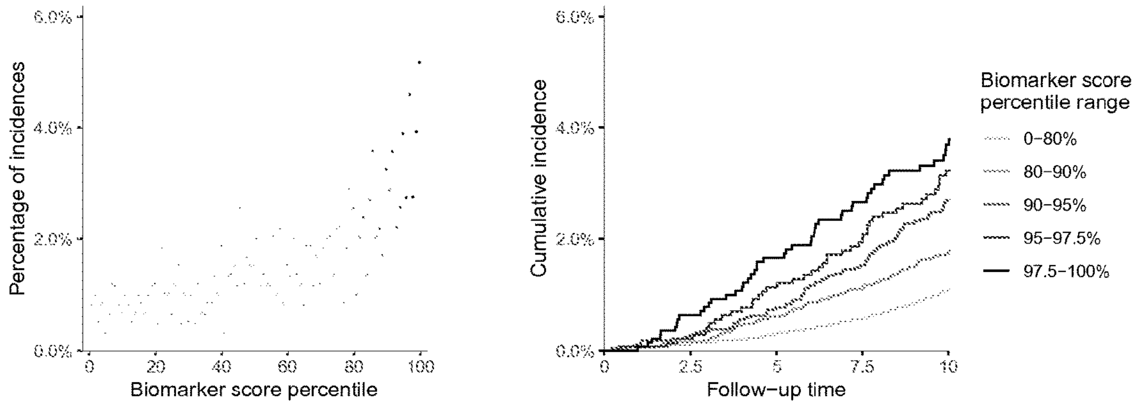
FIG. 13*a* shows an intended use case for a multi-biomarker score to predict the risk for developing symptoms and signs involving cognitive functions and awareness among initially healthy humans.

FIG. 13*a* shows the increase in the risk for symptoms and signs involving cognitive functions and awareness (ICD-10 code R41) along with increasing levels of a multi-biomarker score composed of the weighted sum of 24 biomarkers. On the left-hand side, the risk increase is plotted in the form of gradient percentile plots, showing the proportion of individuals who developed symptoms and signs involving cognitive functions and awareness during follow-up when binning individuals into the percentiles of the biomarker score levels. Each dot corresponds to approximately 500 individuals. In the Kaplan-Meier plots on the right-hand side, the cumulative risk for symptoms and signs involving cognitive functions and awareness during follow-up is illustrated for selected quantiles of the multi-biomarker score. Both plots serve to demonstrate that the risk is increasing non-linearly in the high end of the distribution of the multi-biomarker score. The plots are shown for the validation set part of the study population, i.e. 50% which was not included for derivation of the multi-biomarker score (n=58 575 individuals).

Figure 13B:
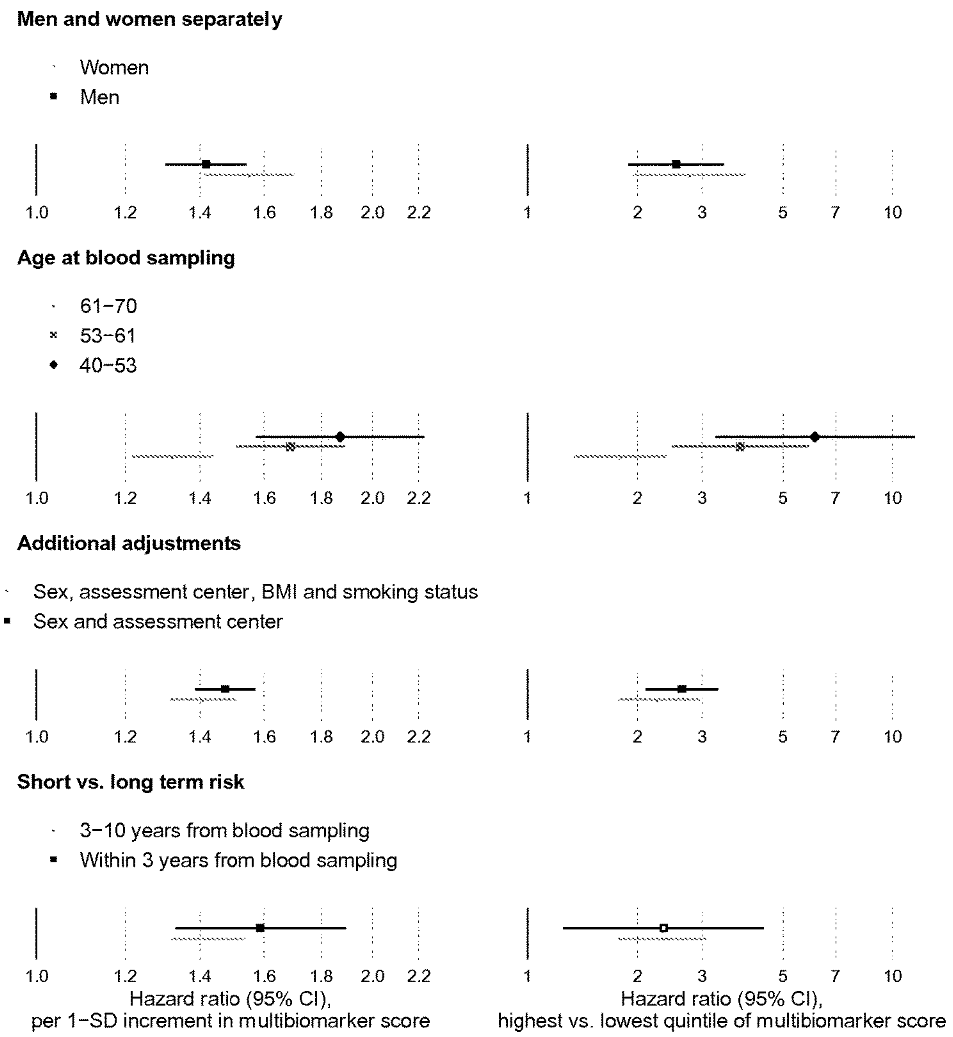
FIG. 13*b* shows that the prediction of the risk for developing symptoms and signs involving cognitive functions and awareness works effectively for people with different demographics and risk factor profiles.

FIG. 13*b* shows the hazard ratio of the same multi-biomarker score with the future onset of symptoms and signs involving cognitive functions and awareness (ICD-10 code R41) when accounting for relevant risk factor characteristics of the study participants. The first panel demonstrates that the risk prediction works effectively for both men and women. The second panel shows that risk prediction also works for people at different ages at the time of blood sampling, with stronger results for younger individuals. The third panel shows that the magnitude of the hazard ratio is only modestly attenuated when accounting for body mass index and smoking status in the statistical modelling. The last panel demontrates that the hazard ratio is stronger when focusing on short-term risk prediction.

It is obvious to a person skilled in the art that with the advancement of technology, the basic idea may be implemented in various ways. The embodiments are thus not limited to the examples described above; instead they may vary within the scope of the claims.

The embodiments described hereinbefore may be used in any combination with each other. Several of the embodiments may be combined together to form a further embodiment. A method disclosed herein may comprise at least one of the embodiments described hereinbefore. It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items. The term "comprising" is used in this specification to mean including the feature(s) or act(s) followed thereafter, without excluding the presence of one or more additional features or acts.

The invention claimed is:

1. A method for determining whether a subject is at risk of developing a mental disorder, the method comprising:

determining in a biological sample obtained from the subject quantitative value(s of at least one biomarker of the following in the biological sample:

glycoprotein acetyls, albumin, a ratio of docosahexaenoic acid to total fatty acids, a ratio of linoleic acid to total fatty acids, a ratio of monounsaturated fatty acids and/or of oleic acid to total fatty acids, a ratio of omega-3 fatty acids to total fatty acids, a ratio of omega-6 fatty acids to total fatty acids, a ratio of saturated fatty acids to total fatty acids, fatty acid degree of unsaturation, docosahexaenoic acid, linoleic acid, monounsaturated fatty acids and/or oleic acid, omega-3 fatty acids, omega-6 fatty acids, saturated fatty acids, triglycerides in high-density lipoprotein (HDL), triglycerides in low-density lipoprotein (LDL), high-density lipoprotein (HDL) particle size, low-density lipoprotein (LDL) particle size, very-low-density lipoprotein (VLDL) particle size, acetate, citrate, glutamine, histidine; and comparing the quantitative value(s) of the at least one biomarker in the biological sample to quantitative value(s) of the at least one biomarker in a control sample or to control values, wherein an increase or a decrease in the quantitative value(s) of the at least one biomarker in the biological sample, when compared to the quantitative value(s) of the at least one biomarker in the control sample or to the control value, is/are indicative of the subject having an increased risk of developing the mental disorder, wherein the at least one biomarker comprises or is glycoprotein acetyls, and the quantitative value of glycoprotein acetyls quantifies a nuclear magnetic resonance spectroscopy signal that represents the abundance of circulating glycated proteins, and wherein the mental disorder is an anxiety disorder; and administering a pharmacological treatment to the subject when the subject is indicated as having the increased risk of developing the mental disorder based on whether there is an increase or a decrease in the quantitative value(s) of the at least one biomarker found in the biological sample.

2. The method according to claim 1, wherein the method comprises determining in the biological sample quantitative values of a plurality of the biomarkers.

3. The method according to claim 1, wherein the method comprises:

determining in the biological sample obtained from the subject the quantitative value(s) of the following biomarkers:

glycoprotein acetyls, and albumin; and comparing the quantitative value(s) of the biomarkers in the biological sample to the quantitative value(s) of the biomarkers in the control sample or to the control value(s);

wherein an increase or a decrease in the quantitative value(s) of the biomarkers in the biological sample, when compared to the quantitative value(s) of the biomarkers in the control sample or to the control value, is/are indicative of the subject having the increased risk of developing the mental disorder.

4. The method according to claim 1, wherein the method comprises determining in the biological sample obtained from the subject the quantitative value(s) of the following biomarkers:

glycoprotein acetyls, and at least one fatty acid measure(s) of the following: ratio of docosahexaenoic acid to total fatty acids, docosahexaenoic acid, ratio of linoleic acid to total fatty acids, linoleic acid, ratio of monounsaturated fatty acids and/or of oleic acid to total fatty acids, ratio of omega-6 fatty acids to total fatty acids, omega-6 fatty acids, ratio of saturated fatty acids to total fatty acids, saturated fatty acids, fatty acid degree of unsaturation; and comparing the quantitative value(s) of the biomarkers in the biological sample to the quantitative value(s) of the biomarkers in the control sample or to the control value(s);

wherein an increase or a decrease in the quantitative value(s) of the biomarkers in the biological sample, when compared to the quantitative value(s) of the biomarkers in the control sample or to the control value(s), is/are indicative of the subject having the increased risk of developing the mental disorder.

5. The method according to claim 1, wherein the mental disorder comprises or is phobic anxiety disorder (F40); and/or other anxiety disorder (F41).

6. The method according to claim 1, wherein the quantitative value(s) of the at least one biomarker is/are measured using nuclear magnetic resonance spectroscopy.

7. The method according to claim 1, wherein the method further comprises determining whether the subject is at risk of developing the mental disorder using a risk score, hazard ratio, odds ratio, and/or predicted absolute risk or relative risk calculated on the basis of the quantitative value(s) of the at least one biomarker.

8. The method according to claim 7, wherein the risk score, hazard ratio, odds ratio, and/or predicted relative risk and/or absolute risk is calculated on the basis of at least one further measure.

9. The method according to claim 8, wherein the at least one further measure comprises a characteristic of the subject.

10. The method according to claim 1, wherein the method comprises determining in the biological sample obtained from the subject the quantitative values of the following biomarkers:

glycoprotein acetyls,
albumin,
the ratio of docosahexaenoic acid to total fatty acids,
the ratio of linoleic acid to total fatty acids,
the ratio of monounsaturated fatty acids and/or of oleic acid to total fatty acids,
the ratio of omega-3 fatty acids to total fatty acids,
the ratio of omega-6 fatty acids to total fatty acids,
the ratio of saturated fatty acids to total fatty acids,
fatty acid degree of unsaturation,
docosahexaenoic acid,
linoleic acid,
monounsaturated fatty acids and/or oleic acid,
omega-3 fatty acids,
omega-6 fatty acids,
saturated fatty acids,
triglycerides in high-density lipoprotein (HDL),
triglycerides in low-density lipoprotein (LDL),
high-density lipoprotein (HDL) particle size,
low-density lipoprotein (LDL) particle size,
very-low-density lipoprotein (VLDL) particle size,
acetate,
citrate,
glutamine, and
histidine; and comparing the quantitative values of the biomarkers in the biological sample to the quantitative values of the biomarkers in the control sample or to the control values;

wherein an increase or a decrease in the quantitative values of the biomarkers in the biological sample, when compared to the quantitative values of the biomarkers in the control sample or to the control values, is/are indicative of the subject having the increased risk of developing the mental disorder.

11. The method according to claim 2, wherein the method comprises determining in the biological sample quantitative values of three or more biomarkers.

12. The method according to claim 2, wherein the method comprises determining in the biological sample quantitative values of four or more biomarkers.

13. The method according to claim 2, wherein the method comprises determining in the biological sample quantitative values of five or more biomarkers.

14. The method according to claim 9, wherein the characteristic of the subject includes one or more of age, height, weight, body mass index, race or ethnic group, smoking, and/or family history of mental and/or behavioural disorders of the subject.

15. The method according to claim 1, wherein the pharmacological treatment comprises an antidepressant, a psychosomatic medicine, a mood stabilizer, a mood stimulant, or a combination thereof.

16. The method according to claim 15, wherein the pharmacological treatment comprises a cholinesterase inhibitor.

* * * * *